US012680286B2

(12) United States Patent
Terada et al.

(10) Patent No.: US 12,680,286 B2
(45) Date of Patent: Jul. 14, 2026

(54) TOILET DEVICE, METHOD FOR CONTROLLING A TOILET DEVICE, AND CONTROL PROGRAM OF A TOILET DEVICE

(71) Applicant: TOTO LTD., Kitakyushu (JP)

(72) Inventors: Yutaro Terada, Kitakyushu (JP);
Satoshi Kawada, Kitakyushu (JP);
Takamasa Suzuki, Kitakyushu (JP);
Junki Hamada, Kitakyushu (JP);
Takaaki Gondo, Kitakyushu (JP);
Takashi Matsunaga, Kitakyushu (JP)

(73) Assignee: TOTO LTD., Kitakyushu (JP)

( * ) Notice: Subject to any disclaimer, the term of this patent is extended or adjusted under 35 U.S.C. 154(b) by 343 days.

(21) Appl. No.: 18/599,730

(22) Filed: Mar. 8, 2024

(65) Prior Publication Data

US 2024/0328136 A1 Oct. 3, 2024

(30) Foreign Application Priority Data

Mar. 31, 2023 (JP) ................................. 2023-058678

(51) Int. Cl.
E03D 9/00 (2006.01)
G01N 33/493 (2006.01)
H04W 4/30 (2018.01)

(52) U.S. Cl.
CPC ............. E03D 9/00 (2013.01); G01N 33/493 (2013.01); H04W 4/30 (2018.02)

(58) Field of Classification Search
CPC .......... E03D 9/00; H04W 4/30; G01N 33/493
USPC .......................................................... 4/300
See application file for complete search history.

(56) References Cited

U.S. PATENT DOCUMENTS

| | | | | |
|---|---|---|---|---|
| 8,364,546 B2 * | 1/2013 | Yenni | ...................... | H04L 67/12 |
| | | | | 702/56 |
| 10,383,606 B1 * | 8/2019 | McCord | ............... | G01N 1/2035 |
| 2013/0250826 A1 | 9/2013 | Tanizawa et al. | | |
| 2017/0322197 A1 * | 11/2017 | Hall | ...................... | G01N 33/493 |
| 2019/0147731 A1 | 5/2019 | Herdt et al. | | |
| 2020/0205717 A1 | 7/2020 | Yang et al. | | |
| 2023/0012841 A1 * | 1/2023 | Yamada | .................... | E03D 9/00 |
| 2024/0324879 A1 * | 10/2024 | Terada | ................. | A61B 5/6891 |
| 2024/0328135 A1 * | 10/2024 | Terada | ................. | G01N 33/493 |

FOREIGN PATENT DOCUMENTS

| | | |
|---|---|---|
| JP | 2001-140325 A | 5/2001 |
| JP | 2013-200785 A | 10/2013 |
| JP | 2020-187089 A | 11/2020 |
| JP | 2020-200753 A | 12/2020 |
| JP | 2021-501329 A | 1/2021 |
| JP | 2023-044234 A | 3/2023 |

* cited by examiner

*Primary Examiner* — Huyen D Le
(74) *Attorney, Agent, or Firm* — McDonald Hopkins LLC

(57) ABSTRACT

A toilet device includes a toilet unit including a toilet seat, a biological information measuring part configured to measure biological information of a user, a wireless communication part configured to wirelessly communicate with a personal digital assistant of the user, and a controller configured to transmit the biological information to the personal digital assistant of the user; the controller is configured to provide the transmission suspension period between a start of the user using the toilet unit and a transmission of the biological information; and the controller is configured to set the transmission period when transmitting the biological information.

6 Claims, 15 Drawing Sheets

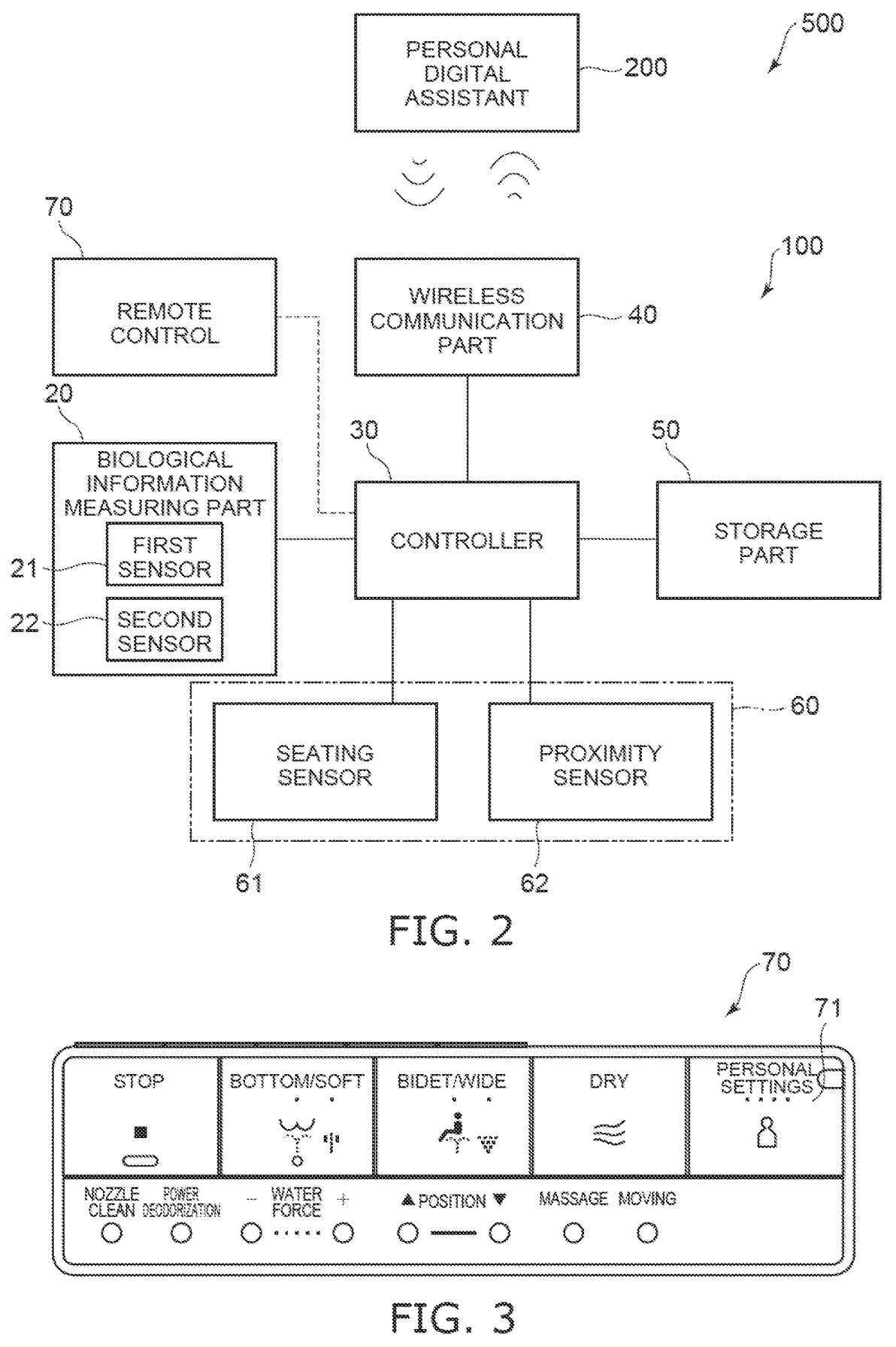

500

PERSONAL DIGITAL ASSISTANT — 200

100

70

REMOTE CONTROL

WIRELESS COMMUNICATION PART — 40

20

30

50

BIOLOGICAL INFORMATION MEASURING PART

CONTROLLER

STORAGE PART

21 — FIRST SENSOR

22 — SECOND SENSOR

60

SEATING SENSOR

PROXIMITY SENSOR

| STOP | BOTTOM/SOFT | BIDET/WIDE | DRY | PERSONAL SETTINGS |
|---|---|---|---|---|

NOZZLE CLEAN   POWER DEODORIZATION    − WATER FORCE +    ▲ POSITION ▼    MASSAGE   MOVING

FIG. 3

TOILET DEVICE, METHOD FOR CONTROLLING A TOILET DEVICE, AND CONTROL PROGRAM OF A TOILET DEVICE

CROSS-REFERENCE TO RELATED APPLICATIONS

This application is based upon and claims the benefit of priority from Japanese Patent Application No. 2023-058678, filed on Mar. 31, 2023; the entire contents of which are incorporated herein by reference.

FIELD

Embodiments described herein relate generally to a toilet device, a method for controlling a toilet device, and a control program of a toilet device.

BACKGROUND

There is a toilet device that measures biological information such as the pulsatory motion, excrement condition, etc., of a user and transmits the measurement result to a personal digital assistant of the user via wireless communication (e.g., 2020-187089 JP A). To improve the convenience of the user of such a toilet device, it is desirable for the measurement result to be automatically transmitted to the personal digital assistant without the user performing a special operation.

For example, automatic transmission of the measurement result to the personal digital assistant is being investigated in which an activation signal is transmitted from a toilet device to a personal digital assistant to activate prescribed application software, which is preinstalled in the personal digital assistant, in the background without requiring a user operation.

However, according to such a method, if the user performs a so-called task-kill that manually ends the application software activated in the background, there is a possibility that the personal digital assistant may no longer respond to subsequent activation signals; and the application software may no longer be re-activated.

To recover from the state in which the personal digital assistant does not respond to the activation signal without operating the personal digital assistant, a state in which the activation signal is not received must be continued for not less than a prescribed period. Therefore, if the toilet device is regularly transmitting the activation signal, it would be necessary to move once out of the range of communication of the toilet device (e.g., outside the toilet room).

It also may be considered that the user could operate the personal digital assistant, etc., to activate the application software to manually establish wireless communication with the toilet device, but this would undesirably require time and effort of the user.

Thus, when the personal digital assistant no longer responds to the activation signal, the user must take action such as moving once out of the range of communication or manually establishing wireless communication, which undesirably requires time and effort of the user. If the user does not take such action, the transmission of the measurement result is undesirably carried over to a subsequent use.

Because defecation is a natural part of daily life (the user cannot intentionally defecate), the measurement result should be acquirable automatically without requiring the intention of the user. Rather than receiving the measurement result at a fixed time, it is desirable for the measurement result to be acquirable as close as possible to the timing of the defecation because defecation is not performed at fixed times and frequency throughout the day.

It is therefore desirable for a toilet device that transmits biological information to a personal digital assistant of a user via wireless communication to be able to more appropriately transmit the biological information to the personal digital assistant of the user.

SUMMARY

According to the embodiment, a toilet device includes a toilet unit including a toilet seat, a biological information measuring part configured to measure biological information of a user, a wireless communication part configured to wirelessly communicate with a personal digital assistant of the user, and a controller configured to transmit the biological information to the personal digital assistant of the user; the personal digital assistant includes an active state in which an application software is activated, and an inactive state in which the application software is suspended; the personal digital assistant is configured to receive the biological information by wirelessly communicating with the wireless communication part in the active state; the controller is configured to allow the biological information to be automatically transmitted to the personal digital assistant by switching the personal digital assistant from the inactive state to the active state by transmitting an activation signal from the wireless communication part to the personal digital assistant; the activation signal is for switching the personal digital assistant from the inactive state to the active state; the controller is configured to control switching between a transmission period in which the activation signal is transmitted, and a transmission suspension period in which the transmission of the activation signal is suspended; the controller is configured to provide the transmission suspension period between a start of the user using the toilet unit and a transmission of the biological information; and the controller is configured to set the transmission period when transmitting the biological information.

BRIEF DESCRIPTION OF THE DRAWINGS

FIG. 2 is a block diagram schematically illustrating the toilet system including the toilet device according to the embodiment;

FIG. 3 is a front view schematically illustrating a remote control of the toilet device according to the embodiment;

DETAILED DESCRIPTION

Figure 1:
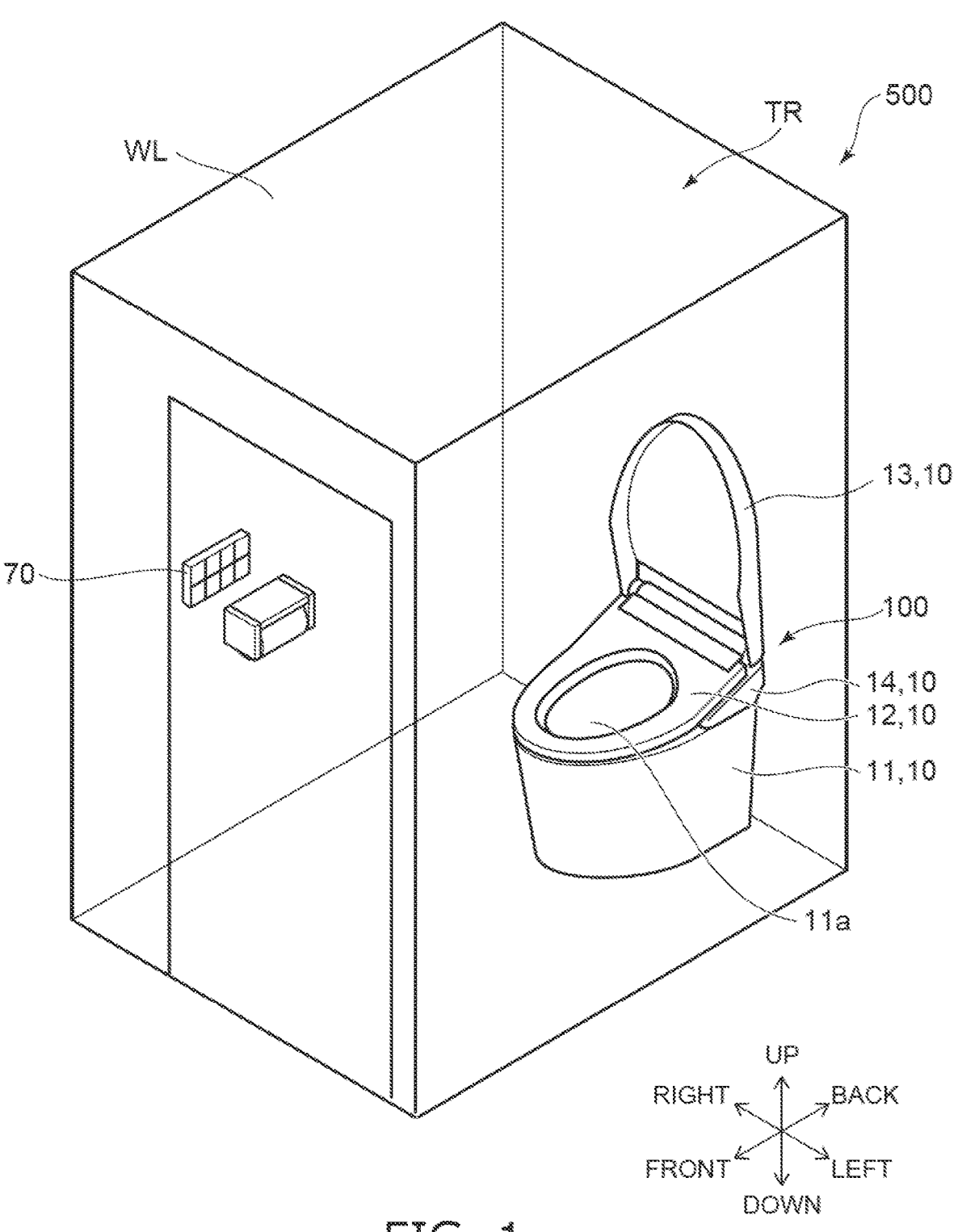
FIG. 1 is a perspective view schematically illustrating a toilet system including a toilet device according to an embodiment.

A first aspect is a toilet device that includes a toilet unit including a toilet seat, a biological information measuring part configured to measure biological information of a user, a wireless communication part configured to wirelessly communicate with a personal digital assistant of the user, and a controller configured to transmit the biological information to the personal digital assistant of the user; the personal digital assistant includes an active state in which an application software is activated, and an inactive state in which the application software is suspended; the personal digital assistant is configured to receive the biological information by wirelessly communicating with the wireless communication part in the active state; the controller is configured to allow the biological information to be automatically transmitted to the personal digital assistant by switching the personal digital assistant from the inactive state to the active state by transmitting an activation signal from the wireless communication part to the personal digital assistant; the activation signal is for switching the personal digital assistant from the inactive state to the active state; the controller is configured to control switching between a transmission period in which the activation signal is transmitted, and a transmission suspension period in which the transmission of the activation signal is suspended; the controller is configured to provide the transmission suspension period between a start of the user using the toilet unit and a transmission of the biological information; and the controller is configured to set the transmission period when transmitting the biological information.

According to the toilet device, by providing the transmission suspension period between the start of the user using the toilet unit and the transmission of the biological information, a state in which the personal digital assistant does not respond to the activation signal can be resolved by the transmission suspension period, even when a task-kill is performed before the biological information is transmitted. Accordingly, when transmitting the biological information, the undesirable state in which the personal digital assistant does not respond to the activation signal can be suppressed. By setting the transmission period when transmitting the biological information, the personal digital assistant can be switched more appropriately to the active state when transmitting the biological information; and the biological information can be transmitted more appropriately and automatically to the personal digital assistant via wireless communication. As a result, the need for the user to take action such as moving once out of the range of communication or manually establishing wireless communication can be suppressed, and the usability can be further improved.

A second aspect is the toilet device of the first aspect, wherein the controller switches from the transmission period to the transmission suspension period for a prescribed period in response to the biological information measuring part completing an acquisition of the biological information.

According to the toilet device, the undesirable state in which the personal digital assistant does not respond to the activation signal when transmitting the biological information due to a task-kill performed before the biological information is transmitted can be more appropriately suppressed.

A third aspect is the toilet device of the second aspect, further including a proximity sensor configured to detect the user approaching the toilet unit and the user leaving the toilet unit; and the controller switches from the transmission period to the transmission suspension period for a prescribed period in response to the proximity sensor detecting the user approaching.

According to the toilet device, by switching from the transmission period to the transmission suspension period for a prescribed period in response to the proximity sensor detecting the user approaching, the personal digital assistant can be switched more promptly to the active state; and by switching from the transmission period to the transmission suspension period for a prescribed period in response to the completion of the acquisition of the biological information, the undesirable state in which the personal digital assistant does not respond to the activation signal when transmitting the biological information can be suppressed, even when a task-kill is performed between detecting the approach and completing the acquisition of the biological information.

A fourth aspect is the toilet device of the second aspect, further including a seating sensor configured to detect the user being seated on the toilet seat and the user leaving the toilet seat; and the controller switches from the transmission period to the transmission suspension period for a prescribed period in response to the seating sensor detecting the user being seated. According to the toilet device, by switching from the transmission period to the transmission suspension period for a prescribed period in response to the seating sensor detecting the user being seated, the personal digital assistant can be switched more promptly to the active state; and by switching from the transmission period to the transmission suspension period for a prescribed period in response to the completion of the acquisition of the biological information, the undesirable state in which the personal digital assistant does not respond to the activation signal when transmitting the biological information can be suppressed, even when a task-kill is performed between detecting the seating and completing the acquisition of the biological information.

A fifth aspect is a method for controlling a toilet device; the toilet device includes a toilet unit including a toilet seat, a biological information measuring part configured to measure biological information of a user, a wireless communication part configured to wirelessly communicate with a personal digital assistant of the user, and a controller configured to transmit the biological information to the personal digital assistant of the user; the personal digital assistant includes an active state in which an application software is activated, and an inactive state in which the application software is suspended; the personal digital assistant is configured to receive the biological information by wirelessly communicating with the wireless communication part in the active state; the controller is configured to allow the biological information to be automatically transmitted to the personal digital assistant by switching the personal digital assistant from the inactive state to the active state by transmitting an activation signal from the wireless communication part to the personal digital assistant; the activation signal is for switching the personal digital assistant from the inactive state to the active state; the controller is configured to control switching between a transmission period in which the activation signal is transmitted, and a transmission suspension period in which the transmission of the activation signal is suspended; and the method includes providing the transmission suspension period between a start of the user using the toilet unit and a transmission of the biological information, and setting the transmission period when the biological information is transmitted.

According to the method for controlling the toilet device, by providing the transmission suspension period between the start of the user using the toilet unit and the transmission of the biological information, the state in which the personal digital assistant does not respond to the activation signal can be resolved by the transmission suspension period, even when a task-kill is performed before the biological information is transmitted. By setting the transmission period when transmitting the biological information, the undesirable state in which the personal digital assistant does not respond to the activation signal when transmitting the biological information can be suppressed. Accordingly, when transmitting the biological information, the personal digital assistant can be switched more appropriately to the active state; and the biological information can be more appropriately and automatically transmitted to the personal digital assistant via wireless communication. As a result, the need for the user to take action such as moving once out of the range of communication or manually establishing wireless communication can be suppressed, and the usability can be further improved.

A sixth aspect is a control program of a toilet device; the control program is installed in the toilet device; the toilet device includes a toilet unit including a toilet seat, a biological information measuring part configured to measure biological information of a user, a wireless communication part configured to wirelessly communicate with a personal digital assistant of the user, and a controller configured to transmit the biological information to the personal digital assistant of the user; the personal digital assistant includes an active state in which an application software is activated, and an inactive state in which the application software is suspended; the personal digital assistant is configured to receive the biological information by wirelessly communicating with the wireless communication part in the active state; the controller is configured to allow the biological information to be automatically transmitted to the personal digital assistant by switching the personal digital assistant from the inactive state to the active state by transmitting an activation signal from the wireless communication part to the personal digital assistant; the activation signal is for switching the personal digital assistant from the inactive state to the active state; the controller is configured to control switching between a transmission period in which the activation signal is transmitted, and a transmission suspension period in which the transmission of the activation signal is suspended; and the control program is configured to cause the toilet device to provide the transmission suspension period between a start of the user using the toilet unit and a transmission of the biological information, and to set the transmission period when the biological information is transmitted.

According to the control program of the toilet device, by providing the transmission suspension period between the start of the user using the toilet unit and the transmission of the biological information, the state in which the personal digital assistant does not respond to the activation signal can be resolved by the transmission suspension period, even when a task-kill is performed before the biological information is transmitted. By setting the transmission period when the biological information is transmitted, the undesirable state in which the personal digital assistant does not respond to the activation signal when transmitting the biological information can be suppressed. Accordingly, when transmitting the biological information, the personal digital assistant can be switched more appropriately to the active state; and the biological information can be more appropriately and automatically transmitted to the personal digital assistant via wireless communication. As a result, the need for the user to take action such as moving once out of the range of communication or manually establishing wireless communication can be suppressed, and the usability can be further improved.

Embodiments of the invention will now be described with reference to the drawings. Similar components in the drawings are marked with the same reference numerals; and a detailed description is omitted as appropriate.

Toilet Device

FIG. 1 is a perspective view schematically illustrating a toilet system including a toilet device according to an embodiment.

FIG. 2 is a block diagram schematically illustrating the toilet system including the toilet device according to the embodiment.

FIG. 3 is a front view schematically illustrating a remote control of the toilet device according to the embodiment.

As illustrated in FIGS. 1 to 3, the toilet system 500 according to the embodiment includes the toilet device 100 and a personal digital assistant 200.

The toilet device 100 includes a toilet unit 10, a biological information measuring part 20, a controller 30, a wireless communication part 40, a storage part 50, a human body detection sensor 60, and a remote control 70. The toilet device 100 is disposed inside a toilet room TR. The toilet room TR may be a toilet room in a general household, or may be a private room (a so-called toilet booth disposed in the restroom of a public facility).

The toilet unit 10 includes a toilet 11, a toilet seat 12, a toilet lid 13, and a casing 14. The toilet 11 is a western-style sit-down toilet. The toilet 11 includes a concave bowl 11a that is recessed downward. The bowl 11a receives human waste, urine, etc., excreted from the user. The toilet unit 10 may not always include the toilet 11. The toilet device 100 may be a toilet device that includes the toilet 11 by being integrated with a toilet, or may be a seat-type toilet device detachably mounted on a toilet.

The toilet seat 12 and the toilet lid 13 each are pivotally supported to be openable and closable with respect to the casing 14. FIG. 1 illustrates a state in which the toilet seat 12 is closed and the toilet lid 13 is open. The toilet lid 13 covers the toilet seat 12 in the closed state from above. The toilet lid 13 is provided as necessary and is omissible. It is sufficient for the toilet unit 10 to include at least the casing 14 and the toilet seat 12 pivotally supported to be openable and closable with respect to the casing 14.

The casing 14 stores various functional units. For example, an automatic opening/closing unit automatically opening and closing the toilet seat 12 and/or the toilet lid 13, a private part washing unit including a nozzle for washing a private part of the user, a private part drying unit for drying a private part of the user, a deodorizing unit that deodorizes, etc., are stored inside the casing 14. These various functional units are provided as necessary and are omissible. The controller 30, the wireless communication part 40, the storage part 50, etc., are stored inside the casing 14.

The biological information measuring part 20 measures biological information of the user. The biological information includes, for example, information related to the user's pulsatory motion, excrement condition, etc. The biological information measuring part 20 is electrically connected with the controller 30. The biological information measuring part 20 communicates with the controller 30 regarding the measured biological information.

The biological information measuring part 20 includes multiple sensors including a first sensor 21 and a second sensor 22. The biological information measuring part 20 uses the multiple sensors 21 and 22 to measure multiple biological information of the user. The first sensor 21 is, for example, a pulsatory motion sensor. More specifically, the first sensor 21 is, for example, a laser sensor. For example, the first sensor 21 is disposed at the toilet seat 12. For example, the first sensor 21 measures the pulsatory motion of the user seated on the toilet seat 12 by using hemoglobin infrared reflection.

The second sensor 22 is, for example, an image sensor. More specifically, the second sensor 22 is, for example, a line sensor in which multiple pixels are arranged in a line shape. The second sensor 22 may be, for example, an area sensor in which multiple pixels are arranged in a matrix configuration. For example, the second sensor 22 is disposed inside the casing 14.

For example, the second sensor 22 determines the excrement condition (the shape, color, amount, etc.) by using image data of the imaged excrement such as feces and the like excreted into the bowl 11*a*.

The measurement of the biological information by the first and second sensors 21 and 22 may include acquiring information by a measurement and analyzing the information acquired by the measurement. As biological information, for example, the first sensor 21 acquires (estimates) information such as the vascular age, lower limb blood circulation status, fitness level, basal metabolism, body water level, body clock, normal heart rate, etc., by analyzing information of the measured pulsatory motion of the user. As biological information, for example, the second sensor 22 acquires (estimates) information of the state of the intestinal environment by analyzing information of the measured excrement condition.

The analysis of the information measured by the first and second sensors 21 and 22 is not limited to the first and second sensors 21 and 22 and may be performed by, for example, the controller 30, the personal digital assistant 200, etc. For example, the analysis of the biological information may be performed by an external server or the like (an external device) by transmitting the biological information from the personal digital assistant 200 of the user to an external server (e.g., a cloud server), etc.

Thus, the biological information that is measured by the first and second sensors 21 and 22 may be measurement information for which only measurement is performed, or may be analysis information acquired by analyzing the measurement information acquired by the measurement.

Each of the first and second sensors 21 and 22 may acquire multiple measurement information by measurement. Each of the first and second sensors 21 and 22 may acquire multiple biological information by analysis. For example, each of the first and second sensors 21 and 22 may acquire multiple biological information from one set of measurement information by analysis. In other words, one sensor disposed in the biological information measuring part 20 may measure multiple biological information.

The multiple biological information that is measured by the multiple sensors of the biological information measuring part 20 is not limited to the biological information described above and may be any information that is associated with the health condition of the user and is acquirable by the toilet device 100. In the example, the biological information measuring part 20 includes two sensors, i.e., the first sensor 21 and the second sensor 22. The number of sensors disposed in the biological information measuring part 20 is not limited to two and may be three or more. It is sufficient for the number of sensors disposed in the biological information measuring part 20 to be appropriately set according to the biological information to be measured.

The controller 30 is electrically connected with the biological information measuring part 20, the wireless communication part 40, the storage part 50, and the human body detection sensor 60. The controller 30 acquires the measurement result (the biological information) of the biological information measuring part 20 and the detection result of the human body detection sensor 60. The controller 30 controls the biological information measuring part 20, the wireless communication part 40, and the storage part 50. For example, the controller 30 controls the start and stop of the measurement of the biological information by the biological information measuring part 20. The controller 30 includes, for example, a main body controller that comprehensively controls the components of the toilet device 100, and a sensor controller that is disposed in the biological information measuring part 20 and controls the operation of the biological information measuring part 20. In other words, a part of the controller 30 may be disposed in the biological information measuring part 20. For example, the start and stop of the measurement of the biological information by the biological information measuring part 20 is controlled by at least one of the main body controller or the sensor controller. The controller 30 is, for example, a control circuit including an IC element. The controller 30 is not limited to one IC element (processor) and may include a combination of multiple IC elements.

The controller 30 is configured to transmit the biological information to the personal digital assistant 200 of the user via the wireless communication part 40. The controller 30 also stores the biological information in the storage part 50. The storage part 50 may include a storage part connected to the main body controller and a storage part connected to the sensor controller. In other words, a part of the storage part 50 may be disposed in the biological information measuring part 20. The biological information may be stored in the storage part of the main body controller and may be stored in the storage part of the sensor controller. The controller 30 erases the biological information stored in the storage part 50 from the storage part 50. The storage and erasure of the biological information in the storage part 50 is described below.

The wireless communication part 40 is configured to connect the controller 30 and the personal digital assistant 200 by wireless communication. The wireless communication part 40 is electrically connected with the controller 30. The wireless communication part 40 is, for example, a communication module configured to communicate using a Bluetooth (registered trademark) standard such as BLE (Bluetooth Low Energy), etc. For example, the wireless communication part 40 is configured to connect the controller 30 and the personal digital assistant 200 positioned inside the toilet room TR by wireless communication.

For example, the connection between the controller 30 and the personal digital assistant 200 is disconnected when the personal digital assistant 200 is outside the toilet room TR. Also, the connection between the controller 30 and the personal digital assistant 200 is disconnected when, for example, a disconnect request signal is transmitted from the personal digital assistant 200. The connection between the toilet device 100 (the controller 30) and the personal digital assistant 200 is described below.

The form of communication between the toilet device 100 and the personal digital assistant 200 is not limited to the toilet device 100 and the personal digital assistant 200 being directly connected by wireless communication and may be, for example, communication via an external server (e.g., a cloud server), etc. The wireless communication part 40 may wirelessly communicate with the external server. For example, the toilet device 100 may transmit the acquired biological information (analysis information) to the external server. In such a case, analysis of the biological information may be performed by the server receiving the biological information from the toilet device 100. The personal digital assistant 200 may receive its own biological information (analysis information) from the server by wirelessly communicating with the server. The timing of the wireless communication of the toilet device 100 with the server may be, for example, when transmitting the biological information (the analysis information), in the user authentication, or both. The timing of the wireless communication of the personal digital assistant 200 with the server may be any timing. Devices used in the communication between the toilet device 100 and the personal digital assistant 200 are not limited to servers and may include other devices. The form of communication between the toilet device 100 and the personal digital assistant 200 may be via any external device.

The storage part 50 is configured to store the information output from the controller 30. The storage part 50 is electrically connected with the controller 30. For example, the storage part 50 stores the biological information. For example, the storage part 50 associates and stores the biological information and user information identifying the user in a state in which user authentication is performed. User authentication is described below.

The storage part 50 associates and stores identification information identifying the personal digital assistant 200 and the user information identifying the user. For example, the information that associates the identification information and the user information may be stored in a storage part disposed in the wireless communication part 40. In other words, a part of the storage part 50 may be disposed in the wireless communication part 40. The identification information is, for example, unique information assigned to the personal digital assistant 200 such as a MAC address, etc. The identification information may be, for example, an ID number, a BD address (a BlueTooth address), pairing information (cryptographic information shared by the toilet device 100 and an application of the personal digital assistant 200 when pairing), etc. The user information is, for example, unique information assigned to each user such as a user number, etc. The user information may be any information that can identify the multiple users. The identification information may be any information that can identify the personal digital assistant 200 of each user. A registration mode in which the identification information and the user information are associated and stored is described below.

The human body detection sensor 60 detects the state of the user. The human body detection sensor 60 includes, for example, at least one of a seating sensor 61 or a proximity sensor 62. For example, the seating sensor 61 is disposed in the toilet seat 12. The seating sensor 61 includes, for example, a capacitive sensor. For example, the seating sensor 61 detects the user being seated on the toilet seat 12 and the user leaving the toilet seat 12. The seating sensor 61 may be, for example, a mechanical switch disposed in the casing 14, etc. The seating sensor 61 may be any sensor that can appropriately detect the user being seated and leaving the seat.

For example, the proximity sensor 62 is disposed inside the casing 14. For example, the proximity sensor 62 detects the user approaching the toilet unit 10 and the user leaving the toilet unit 10. For example, the proximity sensor 62 detects the user entering the toilet room TR and the user exiting the toilet room TR. In other words, the proximity sensor 62 is a room entrance detection sensor.

The proximity sensor 62 includes a nondetection state in which the user is not detected, and a detection state in which the user is detected. In other words, the nondetection state is the state in which the user exiting the toilet room TR is detected. In other words, the detection state is the state in which the user entering the toilet room TR is detected.

The proximity sensor 62 includes, for example, at least one of a radio wave sensor or an infrared sensor. However, the proximity sensor 62 is not limited to such sensors and may be any sensor that can appropriately detect the user approaching. The proximity sensor 62 is not limited to a sensor detecting the user entering the toilet room TR and may be a sensor detecting the user approaching the toilet seat 12, the casing 14, or the like of the toilet unit 10. The proximity sensor 62 may be disposed outside the casing 14.

For example, the remote control 70 is disposed at a wall surface WL of the toilet room TR. The remote control 70 is an operation unit for remotely operating various functional units stored inside the casing 14. The operation unit is not limited to the remote control 70 being disposed separately from the casing 14 and may be, for example, integrally provided with the casing 14.

For example, the remote control 70 transmits, to the controller 30, signals for operating the various functional units based on operation input of the remote control 70 by the user. When receiving the signals from the remote control 70, the controller 30 controls the various functional units based on the signals. For example, the remote control 70 is connected with the controller 30 by wireless communication. For example, the wireless communication part that connects the remote control 70 and the controller 30 is disposed separately from the wireless communication part 40.

The remote control 70 (the operation unit) includes, for example, an authentication switch 71 for transmitting an authentication signal. When an operation input of the authentication switch 71 is performed, the remote control 70 transmits the authentication signal to the controller 30. For example, the controller 30 can perform user authentication based on the authentication signal from the remote control 70. The user authentication is described below.

The personal digital assistant 200 is, for example, a smartphone, tablet terminal, or the like possessed by the user. However, the personal digital assistant 200 is not limited to such terminals; any terminal that can be carried by the user may be used.

A control program (application software) for connecting with the toilet device 100 and displaying information (e.g., analysis information) transmitted from the toilet device 100 is preinstalled in the personal digital assistant 200.

The personal digital assistant 200 includes an active state in which the application software is activated, and an inactive state in which the application software is suspended. The personal digital assistant 200 is configured to receive the biological information by wirelessly communicating with the wireless communication part 40 in the active state.

Figure 4:
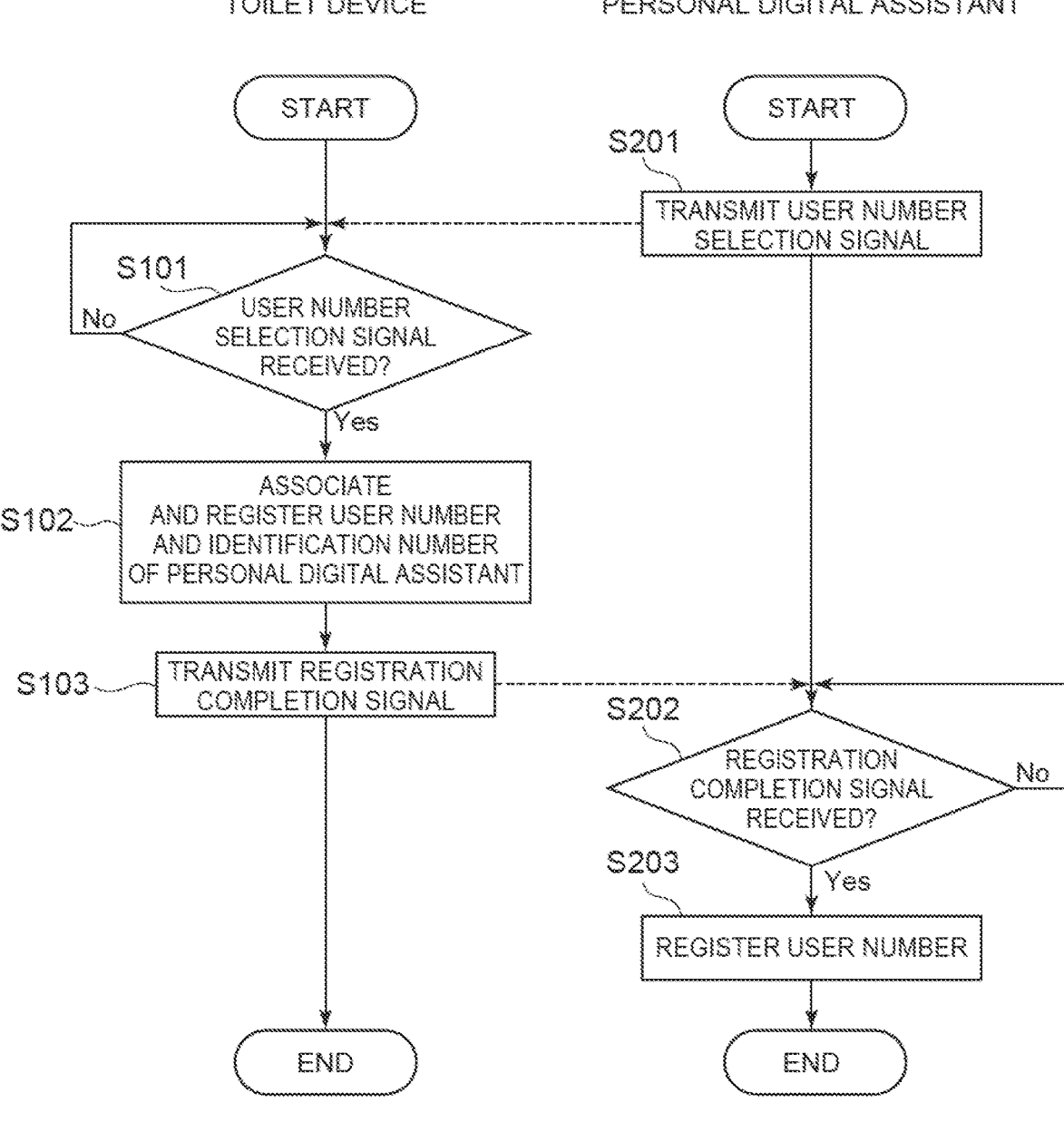
FIG. 4 is a flowchart schematically illustrating an example of an operation of a registration mode of the toilet device and the personal digital assistant according to the embodiment.

FIG. 4 is a flowchart schematically illustrating an example of an operation of a registration mode of the toilet device and the personal digital assistant according to the embodiment.

Figure 5:
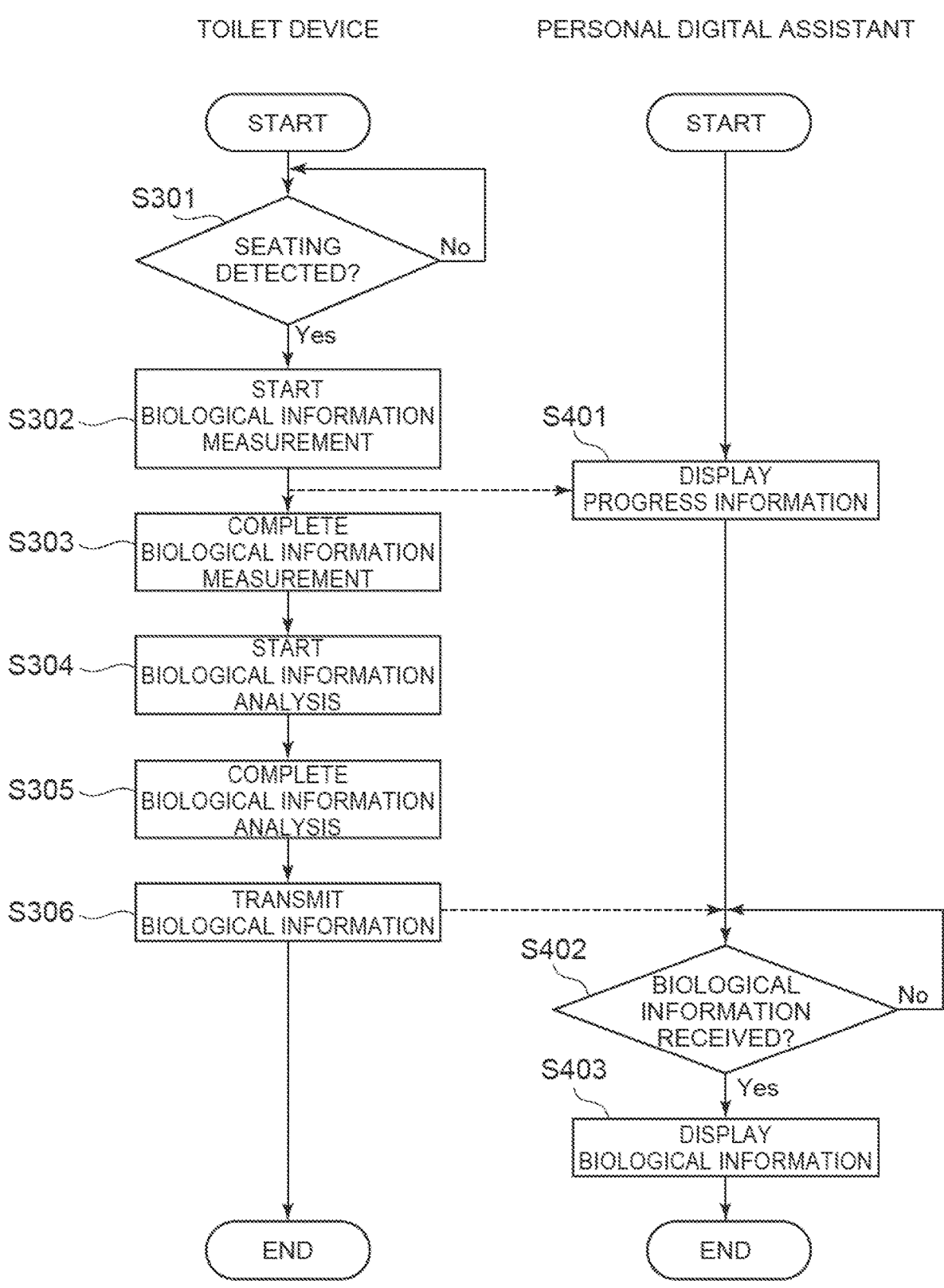
FIG. 5 is a flowchart schematically illustrating an example of an operation of a use mode of the toilet device and the personal digital assistant according to the embodiment.

FIG. 5 is a flowchart schematically illustrating an example of an operation of a use mode of the toilet device and the personal digital assistant according to the embodiment.

As illustrated in FIGS. 4 and 5, the toilet device 100 (the controller 30) includes the registration mode and the use mode.

The registration mode is a mode in which user registration can be performed. User registration is the operation of associating the identification information identifying the personal digital assistant 200 and the user information (e.g., the user number) identifying the user, and storing the identification information and the user information in the storage part 50. The user registration may be performed by storing the identification information and the user information in a storage part disposed in the wireless communication part 40 (a part of the storage part 50 disposed in the wireless communication part 40). The registration mode is performed in a state in which the toilet device 100 (the controller 30) and the personal digital assistant 200 are connected by wireless communication.

The use mode is a mode in which the measurement of the biological information, the analysis of the biological information, and the transmission of the analysis information can be performed. For example, the controller 30 normally operates in the use mode. For example, the controller 30 performs the operation of the registration mode in response to receiving an instruction from the remote control 70 or the personal digital assistant 200 to perform the registration mode during the operation of the use mode. After performing the operation of the registration mode, the controller 30 returns to the operation of the use mode.

When user registration has already been performed, the user authentication can be performed in the use mode. User authentication is the operation of designating the user. In other words, user authentication is the operation of desig- nating the user information (the user number) of the user using the toilet device 100 and the identification information of the personal digital assistant 200 of the user. For example, by performing user authentication, the biological information can be associated with the user information (the user number) and/or the identification information of the personal digital assistant 200 of the user and stored in the storage part 50. By performing user authentication, for example, selective wireless communication can be established between the toilet device 100 and the personal digital assistant 200 designated by the user authentication.

For example, the user authentication is performed by the toilet device 100 (the controller 30) and the personal digital assistant 200 being connected by wireless communication. In such a case, the personal digital assistant 200 that is connected with the toilet device 100 (the controller 30) transmits, to the toilet device 100, an authentication signal including the user information (the user number) registered in the personal digital assistant 200. When receiving the authentication signal, the toilet device 100 determines that the user of the user information (the user number) included in the authentication signal is using the toilet device 100. As a result, the user information (the user number) of the user using the toilet device 100 and the identification information of the personal digital assistant 200 of the user can be designated. The user authentication using the personal digital assistant 200 is described below.

For example, the user authentication may be performed by an operation input of the authentication switch 71 of the remote control 70. In such a case, when the operation input of the authentication switch 71 (e.g., the selection of the user number) is performed, the remote control 70 transmits an authentication signal including the user information (the user number) to the toilet device 100. When receiving the authentication signal, the toilet device 100 determines that the user of the user information (the user number) included in the authentication signal is using the toilet device 100. As a result, the user information (the user number) of the user using the toilet device 100 and the identification information of the personal digital assistant 200 of the user can be designated. The user authentication using the remote control 70 is described below.

Thus, the controller 30 performs the user authentication to designate the user based on the user information stored in the storage part 50. For example, the controller 30 receives the authentication signal including the user information from at least one of the personal digital assistant 200 or the remote control 70 (the operation unit) and performs user authentication to designate the user based on the user information included in the received authentication signal and the user information stored in the storage part 50. For example, when the same user information as the user information included in the received authentication signal is stored in the storage part 50, the controller 30 designates the user indicated by the user information as the current user.

After performing the user authentication, by associating the biological information and user information of the user designated by the user authentication, the controller 30 can transmit the biological information to the personal digital assistant 200 of the user designated based on the identification information associated with the user information and stored in the storage part 50. As a result, the undesirable transmission of the biological information to the personal digital assistant 200 of a different user can be suppressed.

The registration mode will now be described in more detail. In the registration mode as illustrated in FIG. 4, the toilet device 100 (the controller 30) determines whether or not a user number selection signal is received (step S101). The toilet device 100 (the controller 30) repeats step S101 until the user number selection signal is received (step S101: No). The user number selection signal indicates a user number selected by the personal digital assistant 200.

When the user number selection signal is received (step S101: Yes), the toilet device 100 (the controller 30) associates the selected user number and the identification number of the personal digital assistant 200 transmitting the user number selection signal and stores (registers) the selected user number and the identification number in the storage part 50 (step S102).

The user number and the identification number are associated and registered (step S102); and the toilet device 100 (the controller 30) transmits a registration completion signal to the personal digital assistant 200 (step S103). The registration completion signal indicates that the registration is completed.

When the user number is selected by the personal digital assistant 200, the personal digital assistant 200 transmits the user number selection signal to the toilet device 100 (step S201).

When the user number selection signal is transmitted to the toilet device 100 (step S201), the personal digital assistant 200 determines whether or not the registration completion signal is received from the toilet device 100 (step S202). The personal digital assistant 200 repeats step S202 until the registration completion signal is received (step S202: No).

When the registration completion signal is received (step S202: Yes), the personal digital assistant 200 stores (registers) the registered user number (step S203).

The use mode will now be described in more detail.

In the use mode as illustrated in FIG. 5, the toilet device 100 (the controller 30) determines whether or not the seating sensor 61 has detected the user being seated on the toilet seat 12 (step S301). The toilet device 100 (the controller 30) repeats step S301 until the seating sensor 61 detects the user being seated on the toilet seat 12 (step S301: No).

When the seating sensor 61 detects the user being seated on the toilet seat 12 (step S301: Yes), the toilet device 100 (the controller 30) causes the sensors 21 and 22 of the biological information measuring part 20 to start the measurement of biological information (step S302).

When the measurement of the biological information is completed (step S303), the sensors 21 and 22 start analyzing the biological information (step S304). If the user leaving the toilet seat 12 is detected before the measurement is completed, for example, the sensors 21 and 22 end the measurement of the biological information partway through and start analyzing the biological information.

When the analysis of the biological information is completed (step S305), the toilet device 100 (the controller 30) transmits the biological information (the analysis information) obtained by the analysis to the personal digital assistant 200 (step S306). As described above, the transmission of the biological information is performed by the controller 30 via the wireless communication part 40. As described above, the analysis of the biological information may be performed by the controller 30 and/or the personal digital assistant 200. Steps S304 and S305 may be omitted.

For example, the personal digital assistant 200 displays progress information of the measurement of the biological information (step S401). The display of the progress information is described below.

The personal digital assistant 200 determines whether or not the biological information is received (step S402). The personal digital assistant 200 repeats step S402 until the biological information is received (step S402: No).

When the biological information is received (step S402: Yes), the personal digital assistant 200 displays the biological information (step S403). The personal digital assistant 200 may store the biological information to be able to display the biological information even after the connection between the toilet device 100 (the controller 30) and the personal digital assistant 200 is disconnected.

In step S301, the toilet device 100 (the controller 30) may determine whether or not the proximity sensor 62 has detected the user approaching the toilet unit 10, or may determine whether or not the proximity sensor 62 has detected the user entering the toilet room TR. That is, the trigger of the measurement start of the biological information of the toilet device 100 (the controller 30) may be the user being seated on the toilet seat 12, the user approaching the toilet unit 10, or the user entering the toilet room TR. The trigger of the measurement start of the biological information may be, for example, the completion of the user authentication. The trigger of the measurement start of the biological information may be, for example, a change of the state of the biological information measuring part 20. More specifically, a change of the state of the biological information measuring part 20 is, for example, the change of the output of the line sensor (e.g., a falling object detected), a change of the output of the laser sensor, etc.

The connection between the toilet device 100 and the personal digital assistant 200 will now be described in more detail.

Figure 6:
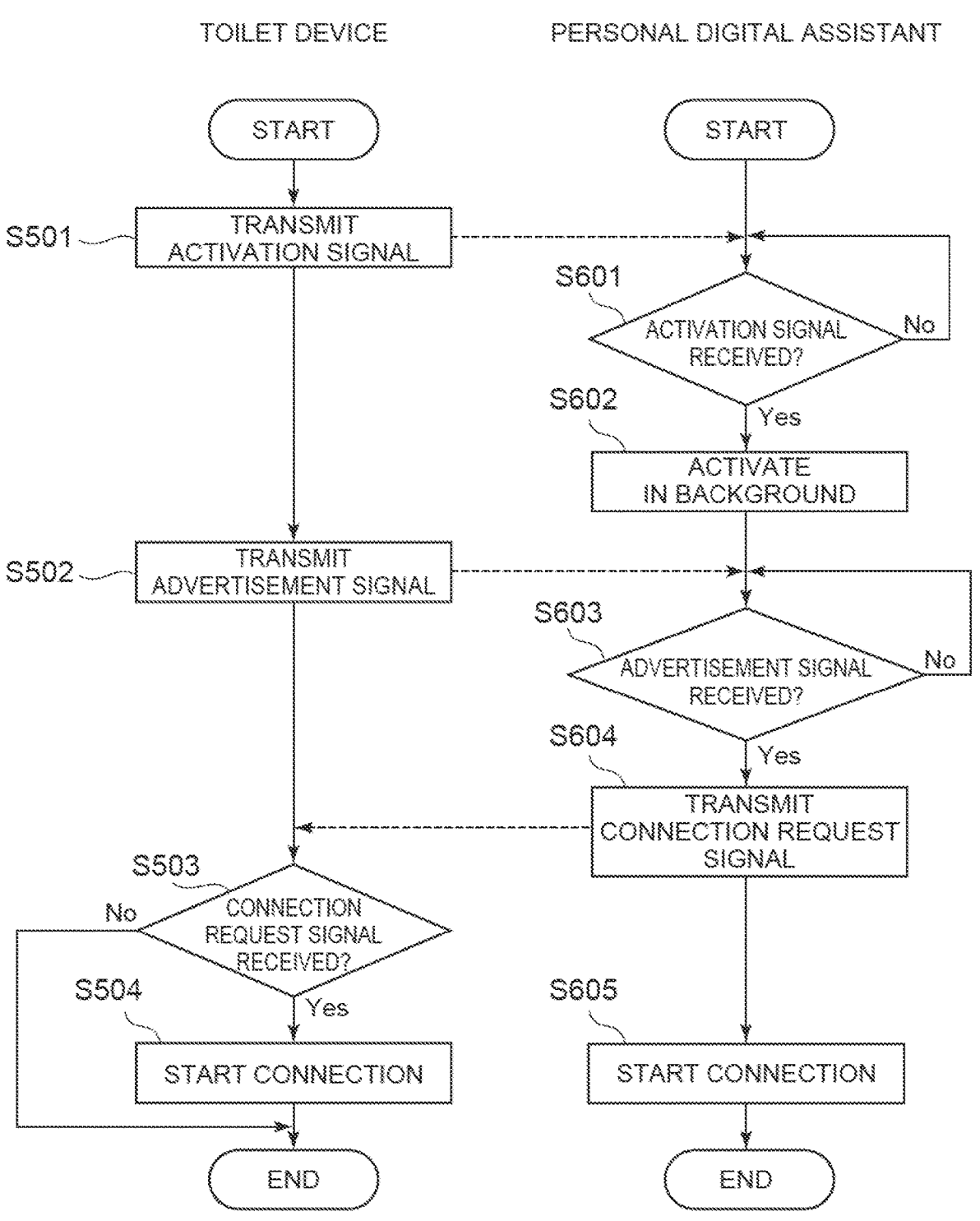
FIG. 6 is a flowchart schematically illustrating an example of an operation when connecting the toilet device and the personal digital assistant according to the embodiment.

FIG. 6 is a flowchart schematically illustrating an example of an operation when connecting the toilet device and the personal digital assistant according to the embodiment.

As illustrated in FIG. 6, the toilet device 100 (the controller 30) transmits an activation signal to the personal digital assistant 200 (step S501). The activation signal is a signal for switching the personal digital assistant 200 from the inactive state to the active state. More specifically, the activation signal is a signal for switching the application software to the active state in the background. In the active state, the personal digital assistant 200 is able to receive an advertisement signal (a wireless signal). In the inactive state, the personal digital assistant 200 cannot receive the advertisement signal (the wireless signal). In other words, the active state is a state in which the advertisement signal can be received. In other words, the inactive state is a state in which the advertisement signal cannot be received.

When transmitting the activation signal (step S501), the toilet device 100 (the controller 30) transmits an advertisement signal to the personal digital assistant 200 (step S502). The advertisement signal is a signal for causing the personal digital assistant 200 to start a connection with the toilet device 100 (the controller 30).

When transmitting the advertisement signal (step S502), the toilet device 100 (the controller 30) determines whether or not a connection request signal is received (step S503). The connection request signal is a signal for causing the toilet device 100 (the controller 30) to start a connection with the personal digital assistant 200.

When receiving the connection request signal (step S503: Yes), the toilet device 100 (the controller 30) starts a connection with the personal digital assistant 200 (step S504). When the connection request signal is not received (step S503: No), the toilet device 100 (the controller 30) does not perform step S504. That is, when the connection request signal is not received (step S503: No), the toilet device 100 (the controller 30) does not start a connection with the personal digital assistant 200.

The personal digital assistant 200 determines whether or not the activation signal is received (step S601). The personal digital assistant 200 repeats step S601 until the activation signal is received (step S601: No).

When the activation signal is received (step S601: Yes), the personal digital assistant 200 switches from the inactive state to the active state (step S602). For example, the personal digital assistant 200 is set to a background active state in which the application software is activated in the background. For example, when the activation signal is received when the user is referring to the screen, etc., the personal digital assistant 200 may activate the application software in the foreground.

In the active state (step S602), the personal digital assistant 200 determines whether or not the advertisement signal is received (step S603). The personal digital assistant 200 repeats step S603 until the advertisement signal is received (step S603: No).

When the advertisement signal is received (step S603: Yes), the personal digital assistant 200 transmits a connection request signal to the toilet device 100 (the controller 30) (step S604) and starts a connection with the toilet device 100 (the controller 30) (step S605).

Thus, the controller 30 switches the personal digital assistant 200 from the inactive state to the active state by transmitting, from the wireless communication part 40 to the personal digital assistant 200, the activation signal for switching the personal digital assistant 200 from the inactive state to the active state. As a result, the controller 30 automatically starts the connection with the personal digital assistant 200 by wireless communication without requiring an operation of the user, etc. As a result, the controller 30 allows the biological information to be automatically transmitted to the personal digital assistant 200. By transmitting the activation signal to automatically start the connection with the personal digital assistant 200 by wireless communication, user authentication that uses the personal digital assistant 200 can be easily performed.

The user authentication using the personal digital assistant 200 will now be described in more detail.

Figure 7:
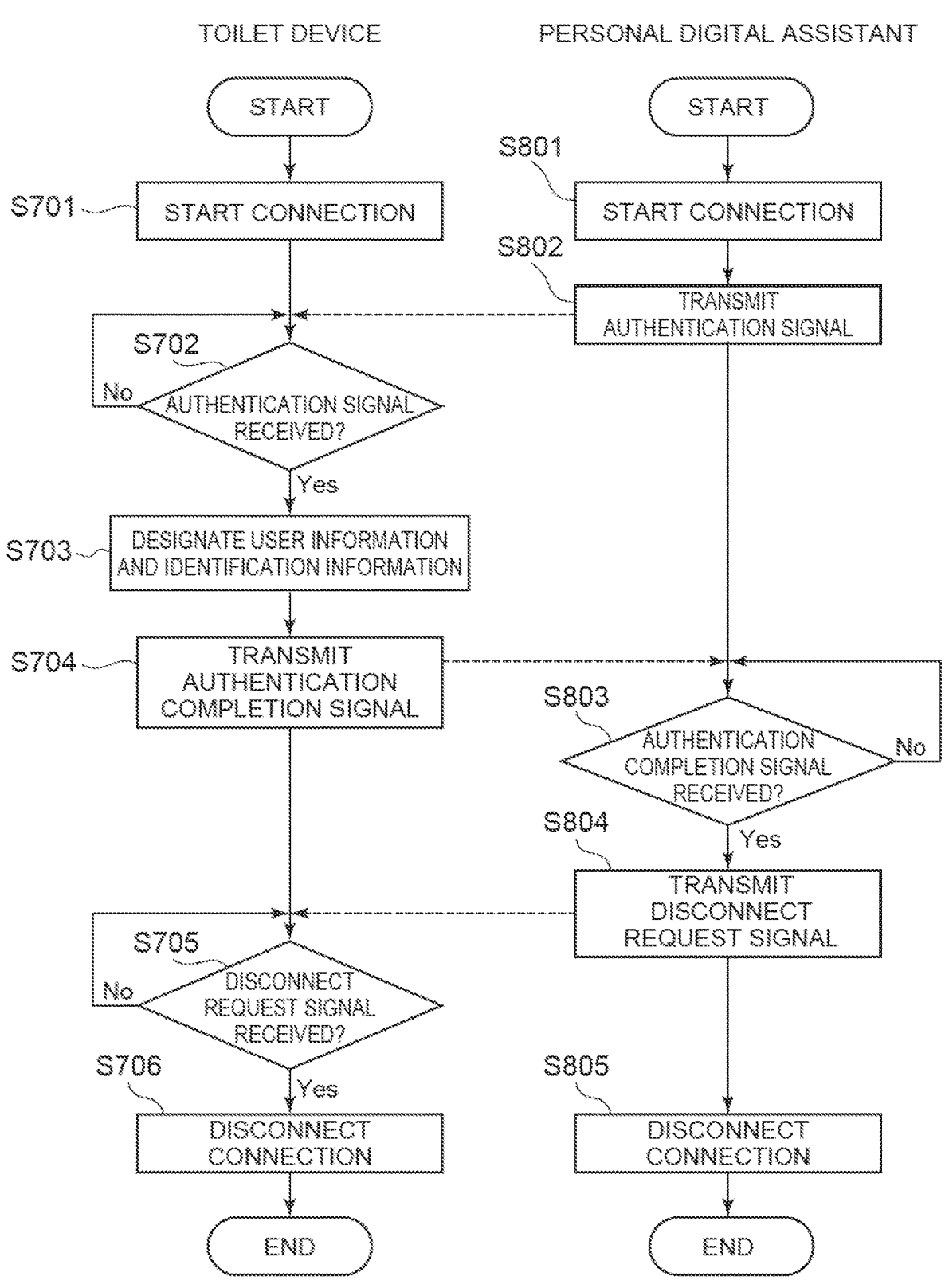
FIG. 7 is a flowchart schematically illustrating an example of an operation in the user authentication of the toilet device and the personal digital assistant according to the embodiment.

FIG. 7 is a flowchart schematically illustrating an example of an operation in the user authentication of the toilet device and the personal digital assistant according to the embodiment.

As illustrated in FIG. 7, when starting the connection with the personal digital assistant 200 (step S701), the toilet device 100 (the controller 30) determines whether or not the authentication signal is received (step S702). The toilet device 100 (the controller 30) repeats step S702 until the authentication signal is received (step S702: No). The authentication signal is, for example, a signal that includes the user information (the user number).

When the authentication signal is received (step S702: Yes), the toilet device 100 (the controller 30) designates the user information and the identification information based on the authentication signal (step S703). More specifically, the toilet device 100 (the controller 30) designates the user information included in the authentication signal and designates the personal digital assistant 200 having the identification information associated with the user information included in the authentication signal.

When the user information and the identification information are designated (step S703), the toilet device 100 (the controller 30) transmits an authentication completion signal to the personal digital assistant 200 (step S704). The authentication completion signal indicates that the user authentication is completed.

When transmitting the authentication completion signal (step S704), the toilet device 100 (the controller 30) determines whether or not a disconnect request signal is received (step S705). The toilet device 100 (the controller 30) repeats step S705 until the disconnect request signal is received (step S705: No). The disconnect request signal is a signal for causing the toilet device 100 (the controller 30) to disconnect the connection with the personal digital assistant 200.

When the disconnect request signal is received (step S705: Yes), the toilet device 100 (the controller 30) disconnects the connection with the personal digital assistant 200 (step S706).

When starting the connection with the toilet device 100 (the controller 30) (step S801), the personal digital assistant 200 transmits the authentication signal (step S802).

When transmitting the authentication signal (step S802), the personal digital assistant 200 determines whether or not the authentication completion signal is received (step S803). The personal digital assistant 200 repeats step S803 until the authentication completion signal is received (step S803: No).

When the authentication completion signal is received (step S803: Yes), the personal digital assistant 200 transmits the disconnect request signal (step S804) and disconnects the connection with the toilet device 100 (the controller 30) (step S805).

Thus, after performing the registration mode (i.e., in the state in which the identification information and the user information are associated and stored in the storage part 50), the toilet device 100 (the controller 30) can perform user authentication in the use mode to designate the user information and the identification information when receiving the authentication signal.

The user authentication using the remote control 70 will now be described in more detail.

Figure 8:
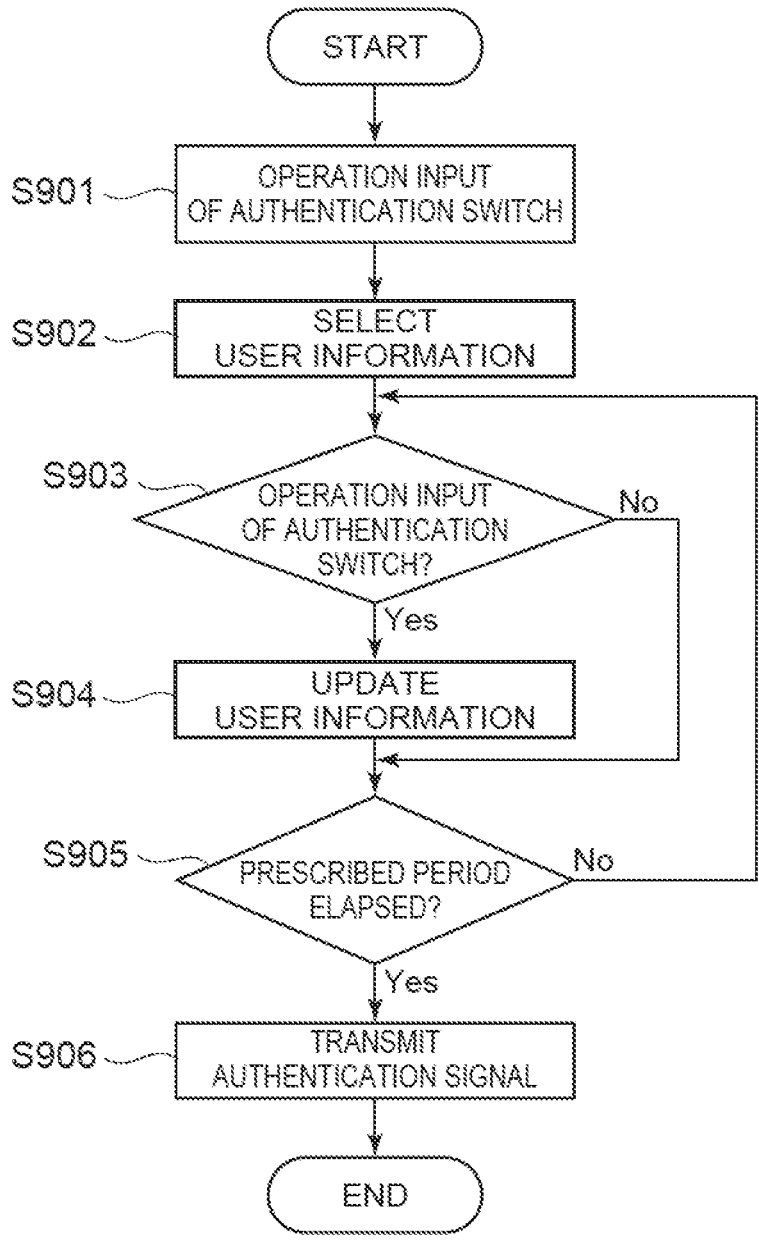
FIG. 8 is a flowchart schematically illustrating an example of an operation in the user authentication of the remote control of the toilet device according to the embodiment.

FIG. 8 is a flowchart schematically illustrating an example of an operation in the user authentication of the remote control of the toilet device according to the embodiment.

As illustrated in FIG. 8, when an operation input of the authentication switch 71 is performed (step S901), the remote control 70 selects user information (step S902). More specifically, the remote control 70 selects, for example, the user number 1 for the first operation input.

When selecting the user information (step S902), the remote control 70 determines whether or not a further operation input of the authentication switch 71 is performed (step S903). When a further operation input of the authentication switch 71 has been performed (step S903: Yes), the remote control 70 updates the user information (step S904). More specifically, for example, the remote control 70 selects the user number 2 when a second operation input is performed. For example, the remote control 70 selects the user number 3 when a third operation input is performed. For example, the remote control 70 selects the user number N when the Nth operation input (N being a natural number) is performed. In other words, for example, the remote control 70 adds 1 to the numerical value of the user number when the operation input is performed. For example, the remote control 70 selects the user number 1 when a further operation input is performed in a state in which the numerical value of the user number has reached an upper limit.

When updating the user information (step S904), the remote control 70 determines whether or not a prescribed period has elapsed from the first operation input (step S905). When the prescribed period has not elapsed from the first operation input (step S905: No), the remote control 70 returns to step S903.

When a further operation input is not performed (step S903: No), the remote control 70 performs step S905 without performing step S904. The remote control 70 repeats step S903, step S904, and step S905 until the prescribed period has elapsed from the first operation input.

When the prescribed period has elapsed from the first operation input (step S905: Yes), the remote control 70 finalizes the user information included in the authentication signal and transmits the authentication signal to the controller 30 (step S906). More specifically, the remote control 70 transmits the authentication signal including the finally-selected user number. As a result, the user authentication can be performed by the remote control 70. In such a case, the user authentication can be performed even when the user is not carrying the personal digital assistant 200, which can improve the convenience of the toilet device 100. For example, the remote control 70 may determine whether or not the prescribed period has elapsed from the previous operation input and may transmit the authentication signal to the controller 30 in response to the elapse of the prescribed period from the previous operation input.

Thus, by including the remote control 70 that transmits the authentication signal, compared to when, for example, the authentication signal is transmitted by operating an operation unit or the like disposed in a location (e.g., the toilet unit 10, etc.) other than the remote control 70, the transmission of the authentication signal (the user authentication) can be performed in a form close to normal use, which is easy-to-use.

The user information for the user authentication can be switched by the number of times one authentication switch 71 is operated by selecting the user information to be designated by the authentication signal based on the number of times that the operation input of the authentication switch 71 is performed until the prescribed period has elapsed, and then transmitting the authentication signal when the prescribed period has elapsed. Misauthentications can be suppressed thereby.

The progress check of the measurement of the biological information will now be described in more detail.

Figure 9:
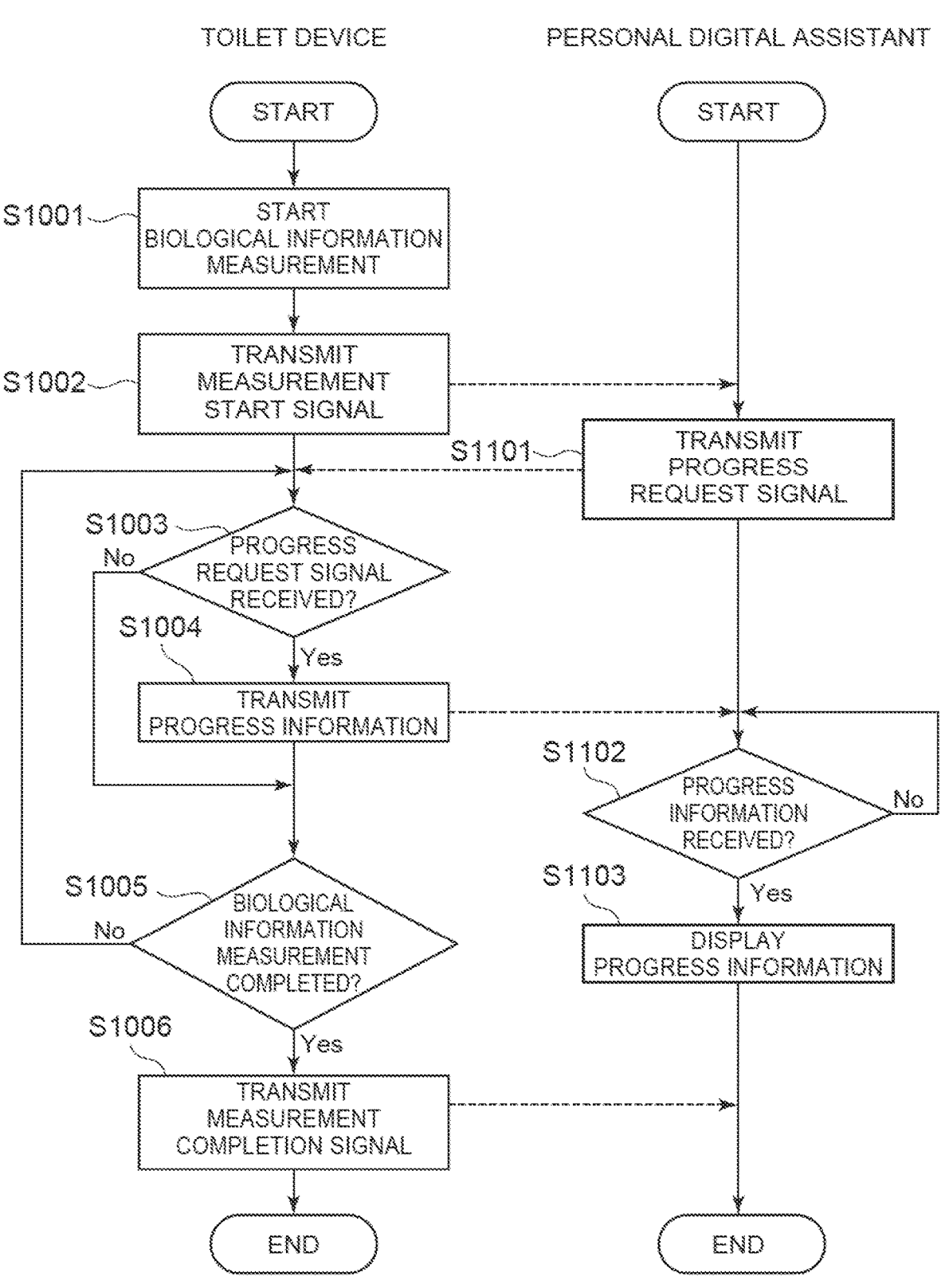
FIG. 9 is a flowchart schematically illustrating an example of an operation of the use mode of the toilet device according to the embodiment.

FIG. 9 is a flowchart schematically illustrating an example of an operation of the use mode of the toilet device according to the embodiment.

As illustrated in FIG. 9, when starting the measurement of the biological information (step S1001), the toilet device 100 (the controller 30) transmits a measurement start signal to the personal digital assistant 200 (step S1002). The measurement start signal indicates that the measurement of the biological information has started.

When transmitting the measurement start signal (step S1002), the toilet device 100 (the controller 30) determines whether or not a progress request signal is received (step S1003). The progress request signal is a signal for causing the toilet device 100 (the controller 30) to transmit progress information. The progress information indicates the progress of the measurement of the biological information. When receiving the progress request signal (step S1003: Yes), the toilet device 100 (the controller 30) transmits the progress information (step S1004).

When transmitting the progress information (step S1004), the toilet device 100 (the controller 30) determines whether or not the measurement of the biological information is completed (step S1005). When the progress request signal is not received (step S1003: No), the toilet device 100 (the controller 30) performs step S1005 without performing step S1004.

When the measurement of the biological information is not completed (step S1005: No), the toilet device 100 (the controller 30) returns to step S1003. The toilet device 100 (the controller 30) repeats step S1003, step S1004, and step S1005 until the measurement of the biological information is completed.

When the measurement of the biological information is completed (step S1005: Yes), the toilet device 100 (the controller 30) transmits a measurement completion signal to the personal digital assistant 200 (step S1006). The measurement completion signal indicates that the measurement of the biological information is completed.

When receiving the measurement start signal, the personal digital assistant 200 is enabled to transmit the progress request signal until the measurement completion signal is received. For example, the personal digital assistant 200 transmits the progress request signal to the toilet device 100 (the controller 30) (step S1101) when an operation input to display the progress information is input to the personal digital assistant 200 while the personal digital assistant 200 is enabled to transmit the progress request signal.

When transmitting the progress request signal (step S1101), the personal digital assistant 200 determines whether or not the progress information is received (step S1102). The personal digital assistant 200 repeats step S1102 until the progress information is received (step S1102: No). When the progress information is received (step S1102: Yes), the personal digital assistant 200 displays the progress information (step S1103).

The personal digital assistant 200 maintains the state of being enabled to transmit the progress request signal until the measurement completion signal is received. When the measurement completion signal is received, the personal digital assistant 200 is set to the state of not being enabled to transmit the progress request signal.

In the example, when the personal digital assistant 200 receives the measurement start signal, the progress information is displayed by the personal digital assistant 200 only while the measurement is being performed by setting the personal digital assistant 200 to a state of being enabled to transmit the progress request signal until the measurement completion signal is received; however, the progress information may be displayed by the personal digital assistant 200 only while the measurement is being performed by enabling the toilet device 100 (the controller 30) to transmit the progress information only while the measurement is being performed. That is, when the measurement is not being performed, the toilet device 100 (the controller 30) may not transmit the progress information even when the progress request signal is received. In such a case, steps S1102 and S1006 are omissible.

The operation of the use mode will now be described in more detail.

Figure 10:
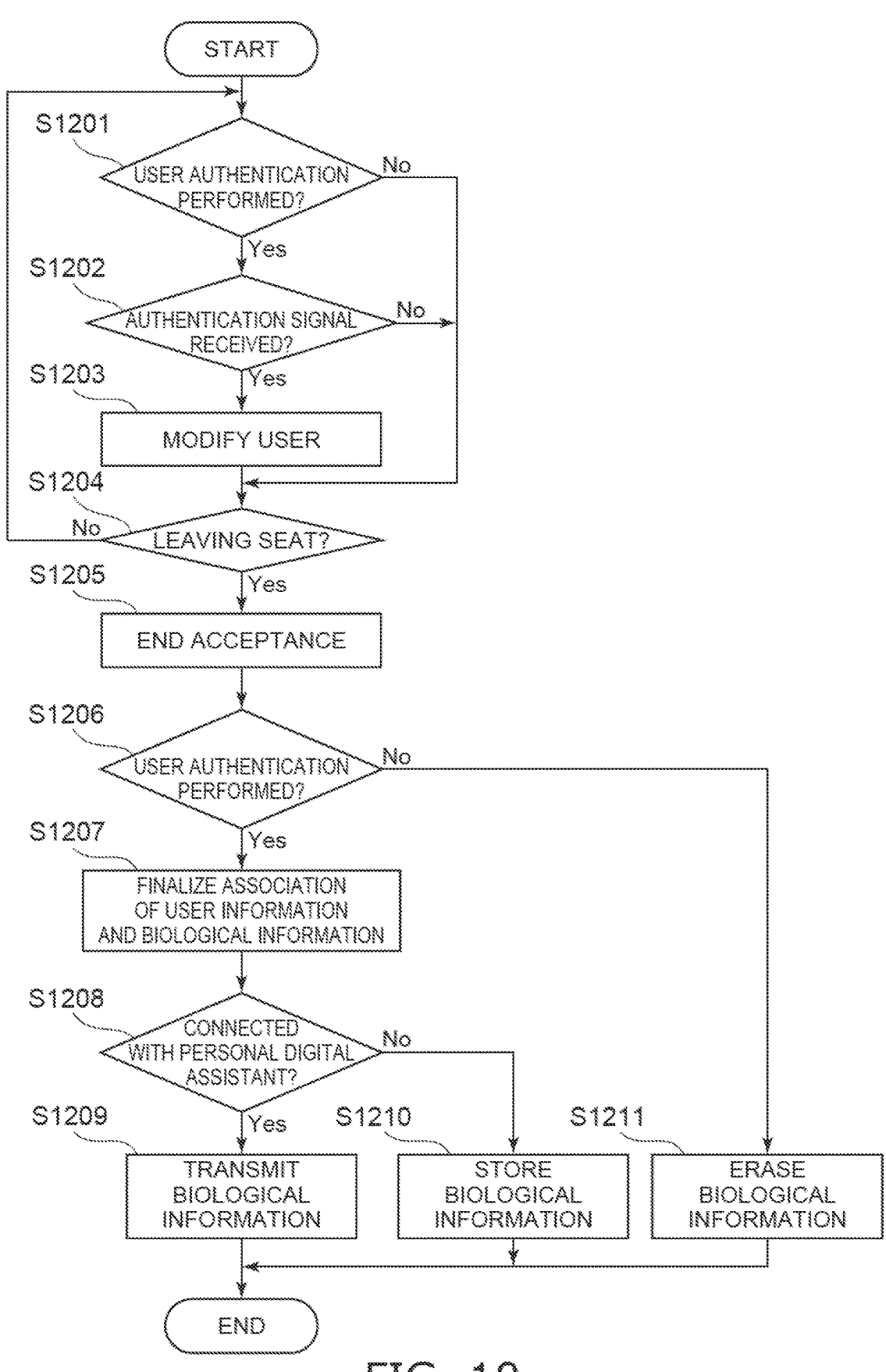
FIG. 10 is a flowchart illustrating an example of an operation of the use mode of the toilet device according to the embodiment.

FIG. 10 is a flowchart illustrating an example of an operation of the use mode of the toilet device according to the embodiment.

In the operation of the use mode as illustrated in FIG. 10, the controller 30 determines whether or not a user authentication has been performed (step S1201). As described above, the controller 30 performs the user authentication by receiving the authentication signal including the user information from at least one of the personal digital assistant 200 or the remote control 70 (the operation unit). When the controller 30 has performed the user authentication and designated the current user, for example, the controller 30 temporarily stores the user information of the designated user as the authentication information in the storage part 50. More specifically, for example, the authentication information is temporarily stored in a storage part connected to the main body controller.

When the controller 30 has performed the user authentication (step S1201: Yes), the controller 30 continues by determining whether or not the authentication signal is received (step S1202). For example, the controller 30 determines whether or not the authentication signal is received from the remote control 70.

When the controller 30 determines that the authentication signal is received from the remote control 70 (step S1202: Yes), the controller 30 modifies the user designated by the user authentication based on the received authentication signal (step S1203).

For example, when the same user information as the user information included in the authentication signal received from the remote control 70 is stored in the storage part 50, the controller 30 modifies the user to the user indicated by the user information included in the received authentication signal. For example, the controller 30 modifies the user designated by the user authentication by modifying the user information of the authentication information temporarily stored in the storage part 50 to the new user information included in the received authentication signal.

When the user authentication has not been performed (step S1201: No), when the authentication signal has not been received (step S1202: No), or when the user has been modified, the controller 30 continues by determining whether or not the seating sensor 61 has detected the user leaving the toilet seat 12 (step S1204).

When the user leaving the toilet seat 12 is not detected, the controller 30 returns to the processing of step S1201. As a result, the controller 30 can perform the user authentication at any timing within a prescribed period in which the user is using the toilet unit 10, and can modify the user designated by the user authentication at any timing within a prescribed period after the user authentication is performed.

The prescribed period is, for example, the period from the timing of the detection of the start of the user using the toilet unit 10 to the timing of the detection of the user leaving the toilet seat 12. In the operation of the use mode as described with reference to FIG. 5, the controller 30 measures the biological information in response to the detection of the user being seated on the toilet seat 12. In other words, the controller 30 performs the user authentication and the modification of the user after the user authentication at any timing in the period from the start of the user using the toilet unit 10 until the biological information is acquired.

The timing of the detection of the start of the user using the toilet unit 10 is, for example, the timing of the proximity sensor 62 detecting the user approaching the toilet unit 10 (entering the toilet room TR). The timing of the detection of the start of the user using the toilet unit 10 may be, for example, the timing of the seating sensor 61 detecting the user being seated on the toilet seat 12. The timing of the detection of the start of the user using the toilet unit 10 may be, for example, the timing of the reception of a signal (e.g., the authentication signal) from the remote control 70. The timing of the detection of the start of the user using the toilet unit 10 may be, for example, the timing at which the wireless communication with the personal digital assistant 200 is established. The timing of the detection of the start of the user using the toilet unit 10 is not limited to the timing described above and may be any timing at which the controller 30 can appropriately detect the start of the user using the toilet unit 10.

The timing of the end of the prescribed period is not limited to the timing of the detection of leaving the seat and may be, for example, the timing when a prescribed period has elapsed from the seating sensor 61 detecting the user leaving the toilet seat 12. The timing of the end of the prescribed period may be, for example, the timing of the proximity sensor 62 detecting the user leaving the toilet unit 10 (exiting the toilet room TR). The timing of the end of the prescribed period may be, for example, the timing at which the connection with the personal digital assistant 200 by wireless communication is disconnected (the timing of the personal digital assistant 200 leaving the communication range). The timing of the end of the prescribed period may be, for example, the timing of the detection of the washing of the toilet 11. For example, the washing of the toilet 11 can be detected in response to the input of a signal from the remote control 70. The washing of the toilet 11 may be detected by, for example, using a sensor or the like to detect the flow of water inside the toilet 11.

The timing of the end of the prescribed period is not limited to the timing described above and may be any timing at which the controller 30 can appropriately detect the end of the use of the toilet unit 10 by the user.

In response to the seating sensor 61 detecting the user leaving the toilet seat 12, the controller 30 ends the user authentication and the acceptance of a modification of the user designated by the user authentication (step S1205). In such a case, the end of the acceptance may be immediately upon the detection of leaving the seat, or may be after a prescribed period has elapsed from the detection of leaving the seat. Thus, ending the acceptance in response to the detection of leaving the seat includes ending the acceptance at the timing of the detection of leaving the seat and ending the acceptance at the timing at which a prescribed period has elapsed from the detection of leaving the seat.

After ending the user authentication and the acceptance of the modification of the user designated by the user authentication, the controller 30 determines whether or not the user authentication has been performed (step S1206). In other words, the controller 30 determines whether or not finalized user information is stored in the storage part 50 as authentication information.

When the user authentication has been performed (step S1206: Yes), the controller 30 finalizes the association between the user information and the biological information (step S1207). For example, after the detection of leaving the seat, the controller 30 ends the user authentication and the acceptance of the modification of the user and associates the biological information acquired in response to the detection of the user being seated and the user information stored as the authentication information in the storage part 50.

After finalizing the association between the user information and the biological information, the controller 30 determines whether or not the personal digital assistant 200 is connected by wireless communication (step S1208).

When the personal digital assistant 200 is connected by wireless communication (step S1208: Yes), the controller 30 transmits the biological information to the personal digital assistant 200 (step S1209).

When the personal digital assistant 200 is not connected by wireless communication (step S1208: No), the controller 30 stores the biological information in the storage part 50 without transmitting the biological information to the personal digital assistant 200 (step S1210). At this time, the controller 30 associates the biological information and the user information and stores the biological information and the user information in the storage part 50. Thus, after the prescribed period has ended, the controller 30 associates the biological information with the user information and stores the biological information and the user information in the storage part 50. The operation after storing the biological information is described below.

When the user authentication has not been performed (step S1206: No), the controller 30 erases the biological information (step S1211). The controller 30 transmits the biological information to the personal digital assistant 200 or stores (saves) the biological information in the storage part 50 only when the user authentication has been performed. For example, the controller 30 may associate the biological information (the analysis information) and the user information and store the biological information (the analysis information) and the user information in the storage part 50 after the association of the user information and the biological information is finalized regardless of the connection status with the personal digital assistant 200 by wireless communication. In such a case, when connected with the personal digital assistant 200 by wireless communication, the controller 30 may erase the biological information (the analysis information) stored in the storage part 50 in response to the transmission of the biological information (the analysis information) to the personal digital assistant 200 being appropriately completed. For example, the controller 30 may continue to store the biological information in the storage part 50 when a discrepancy occurs when transmitting the biological information, etc.

For example, after transmitting the biological information to the personal digital assistant 200 or storing the biological information in the storage part 50, the controller 30 erases the user information of the authentication information temporarily stored in the storage part 50. In other words, after transmitting the biological information to the personal digital assistant 200 or storing the biological information in the storage part 50, the controller 30 clears the authentication status of the user authentication for which the storage is completed.

An operation of the use mode after storing the biological information will now be described in more detail.

Figure 11:
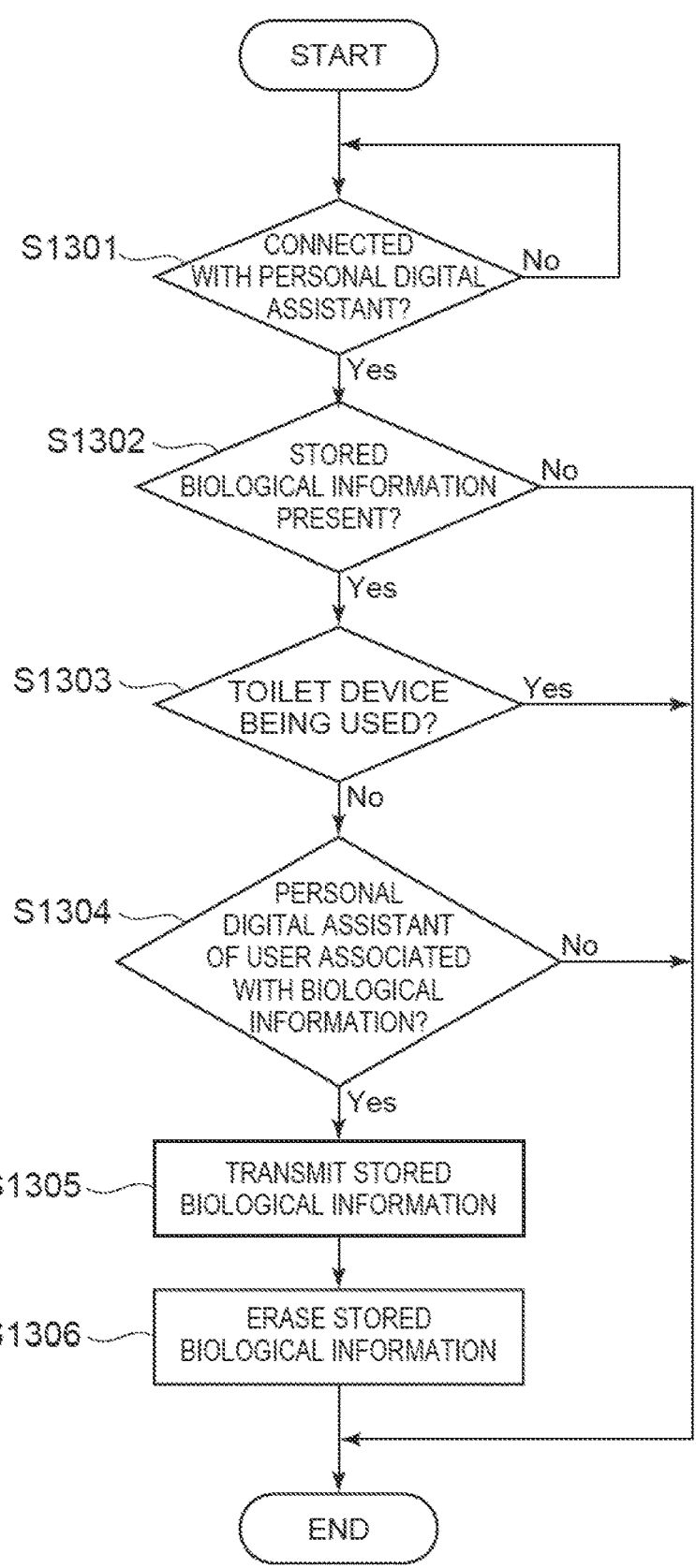
FIG. 11 is a flowchart illustrating an example of an operation of the use mode of the toilet device according to the embodiment.

FIG. 11 is a flowchart illustrating an example of an operation of the use mode of the toilet device according to the embodiment.

As illustrated in FIG. 11, each time the toilet device 100 (the controller 30) is connected with the personal digital assistant 200 (step S1301: Yes), the toilet device 100 (the controller 30) determines whether or not biological information (that is, untransmitted biological information) is stored in the storage part 50 (step S1302). The toilet device 100 (the controller 30) repeats step S1301 until connected with the personal digital assistant 200 (step S1301: No).

When biological information is stored in the storage part 50 (step S1302: Yes), the toilet device 100 (the controller 30) determines whether or not the toilet device 100 is being used (step S1303).

For example, the toilet device 100 (the controller 30) determines that the toilet device 100 is being used when the human body detection sensor 60 detects the user. For example, the toilet device 100 (the controller 30) determines that the toilet device 100 is being used when the seating sensor 61 detects the user seated on the toilet seat 12. For example, the toilet device 100 (the controller 30) determines that the toilet device 100 is being used when the proximity sensor 62 detects the user approaching the toilet unit 10. For example, the toilet device 100 (the controller 30) determines that the toilet device 100 is being used when the proximity sensor 62 detects the user entering the toilet room TR. For example, the toilet device 100 (the controller 30) determines that the toilet device 100 is being used when the biological information measuring part 20 measures the biological information.

When the toilet device 100 is not being used (step S1303: No), the toilet device 100 (the controller 30) determines whether or not the connected personal digital assistant 200 is the personal digital assistant 200 of the user associated with the stored biological information (step S1304). As described above, the biological information is stored after being associated with the user information; and the user information is stored (registered) after being associated with the identification information of the personal digital assistant 200 possessed by the user. Therefore, the biological information that is stored after being associated with the user information is indirectly associated with the identification information that is stored (registered) after being associated with the user information. In other words, the stored biological information is stored after being associated with the identification information of the personal digital assistant 200 to which the biological information is to be transmitted. Here, it is determined whether or not the connected personal digital assistant 200 is the personal digital assistant 200 to which the stored biological information is to be transmitted.

When the connected personal digital assistant 200 is the personal digital assistant 200 of the user associated with the stored biological information (step S1304: Yes), the toilet device 100 (the controller 30) transmits the biological information stored in the storage part 50 to the personal digital assistant 200 (step S1305).

When the biological information stored in the storage part 50 is transmitted to the personal digital assistant 200 (step S1305), the toilet device 100 (the controller 30) erases the stored biological information from the storage part 50 (step S1306).

When no biological information is stored in the storage part 50 (step S1302: No), the toilet device 100 (the controller 30) does not perform step S1303, step S1304, step S1305, and step S1306. When the toilet device 100 is being used (step S1303: Yes), the toilet device 100 (the controller 30) does not perform step S1304, step S1305, and step S1306. When the connected personal digital assistant 200 is not the personal digital assistant 200 of the user associated with the stored biological information (step S1304: No), steps S1305 and S1306 are not performed.

Thus, according to the embodiment, when the analysis of the biological information is completed in a state in which the toilet device 100 (the controller 30) is connected with the personal digital assistant 200 by wireless communication, the toilet device 100 (the controller 30) transmits the biological information to the personal digital assistant 200. When the analysis of the biological information is completed in a state in which the controller 30 is not connected with the personal digital assistant 200 by wireless communication, the controller 30 stores the biological information in the storage part 50 without transmitting the biological information to the personal digital assistant 200. When the controller 30 is connected with the personal digital assistant 200 in a state in which the biological information is stored the storage part 50, the controller 30 transmits the stored biological information to the personal digital assistant 200.

By transmitting the biological information in the personal digital assistant 200 when the analysis of the biological information is completed when the toilet device 100 is connected with the personal digital assistant 200, by storing the biological information in the storage part 50 without transmitting the biological information to the personal digital assistant 200 when the analysis of the biological information is completed when the toilet device 100 is not connected with the personal digital assistant 200, and by transmitting the stored biological information to the personal digital assistant 200 when the toilet device 100 is connected with the personal digital assistant 200 in a state in which the biological information is stored in the storage part 50, even if the analysis of the biological information is not completed when the connection between the toilet device 100 and the personal digital assistant 200 becomes disconnected (e.g., when the user exits the toilet room TR), the biological information can be stored; and the stored biological information can be transmitted to the personal digital assistant 200 the next time the toilet device 100 and the personal digital assistant 200 are connected. As a result, the biological information can be more reliably transmitted to the personal digital assistant 200 of the user; and the ease of use can be improved.

According to the embodiment, for example, when the biological information is stored in the storage part 50 in the state in which the user authentication has been performed, the toilet device 100 (the controller 30) associates the biological information and the user information identifying the user and stores the biological information and the user information in the storage part 50. Then, for example, when connected with the personal digital assistant 200 having identification information that is not associated with the user information in a state in which biological information associated with the user information is stored in the storage part 50, the toilet device 100 (the controller 30) does not transmit the biological information associated with the user information to the personal digital assistant 200 having the identification information not associated with the user information. On the other hand, when connected with the personal digital assistant 200 having identification information associated with the user information in a state in which biological information associated with the user information is stored in the storage part 50, the toilet device 100 (the controller 30) transmits the biological information associated with the user information to the personal digital assistant having the identification information associated with the user information.

When connected with the personal digital assistant 200 having identification information associated with the user information in a state in which biological information associated with the user information is stored in the storage part 50, by transmitting the biological information (that is, the stored biological information) associated with the user information to the personal digital assistant 200, the transmission of the biological information to a personal digital assistant 200 other than the user's own personal digital assistant 200 can be suppressed, and the biological information can be more reliably transmitted to the personal digital assistant 200 of the user as a privacy precaution. Also, the number of communications can be reduced because the biological information is transmitted only to the user's own personal digital assistant 200.

According to the embodiment, for example, when the wireless communication part 40 is connected with the personal digital assistant 200 in a state in which the biological information is stored in the storage part 50, the toilet device 100 (the controller 30) does not transmit the biological information to the personal digital assistant 200 if the toilet device 100 is being used. On the other hand, when the wireless communication part 40 is connected with the personal digital assistant 200 in a state in which the biological information is stored in the storage part 50, the toilet device 100 (the controller 30) transmits the biological information to the personal digital assistant 200 if the toilet device 100 is not being used.

By not transmitting the biological information to the personal digital assistant 200 if the toilet device 100 is being used when the wireless communication part 40 is connected with the personal digital assistant 200 in a state in which the biological information is stored in the storage part 50, processing other than the transmission of the biological information can be given priority while the toilet device 100 is being used. As a result, for example, the analysis of the biological information of the user that is using the toilet device 100 at that time can be given priority, which can improve the ease of use. When, however, the wireless communication part 40 is connected with the personal digital assistant 200 in a state in which the analysis information is stored in the storage part 50, the toilet device 100 (the controller 30) may transmit the analysis information in the personal digital assistant 200 regardless of whether or not the toilet device 100 is being used.

For example, when the analysis information is stored in the storage part 50, the toilet device 100 (the controller 30) may regularly transmit the user information associated with the biological information. In such a case, when the personal digital assistant 200 receives the same user information as the user information possessed by the personal digital assistant 200 itself, the personal digital assistant 200 may connect with the toilet device 100 by wireless communication and receive the analysis information from the toilet device 100.

An operation of the transmission of the activation signal will now be described in more detail.

Figure 12:
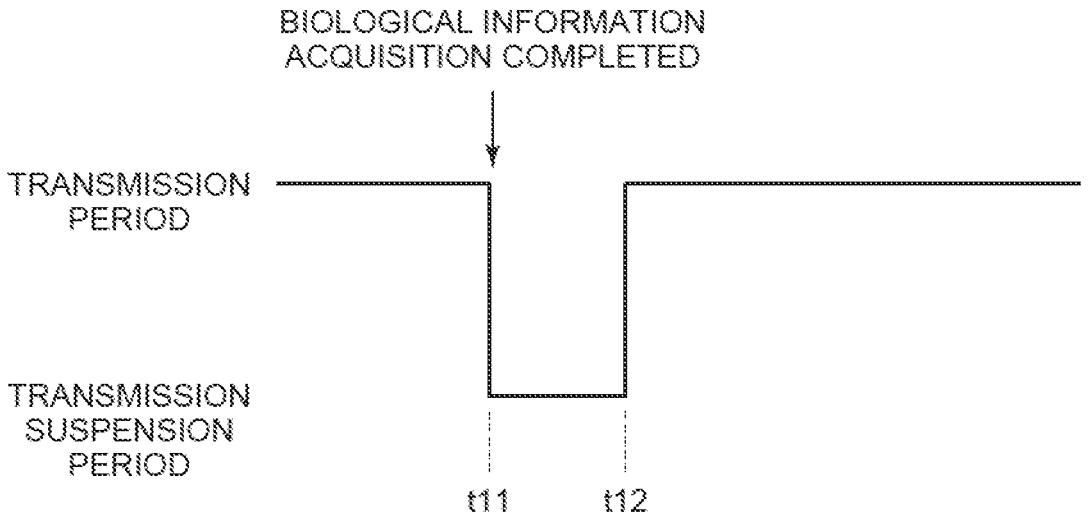
FIG. 12 is a timing chart illustrating an example of the operation of the transmission of the activation signal of the toilet device according to the embodiment.

FIG. 12 is a timing chart illustrating an example of the operation of the transmission of the activation signal of the toilet device according to the embodiment.

As illustrated in FIG. 12, the controller 30 controls switching between a transmission period in which the activation signal is transmitted, and a transmission suspension period in which the transmission of the activation signal is suspended. In the transmission period, for example, the controller 30 transmits the activation signal regularly at a prescribed interval such as an interval of several seconds, etc. Normally, the controller 30 is set to the transmission period in the operation of the use mode.

Figure 13:
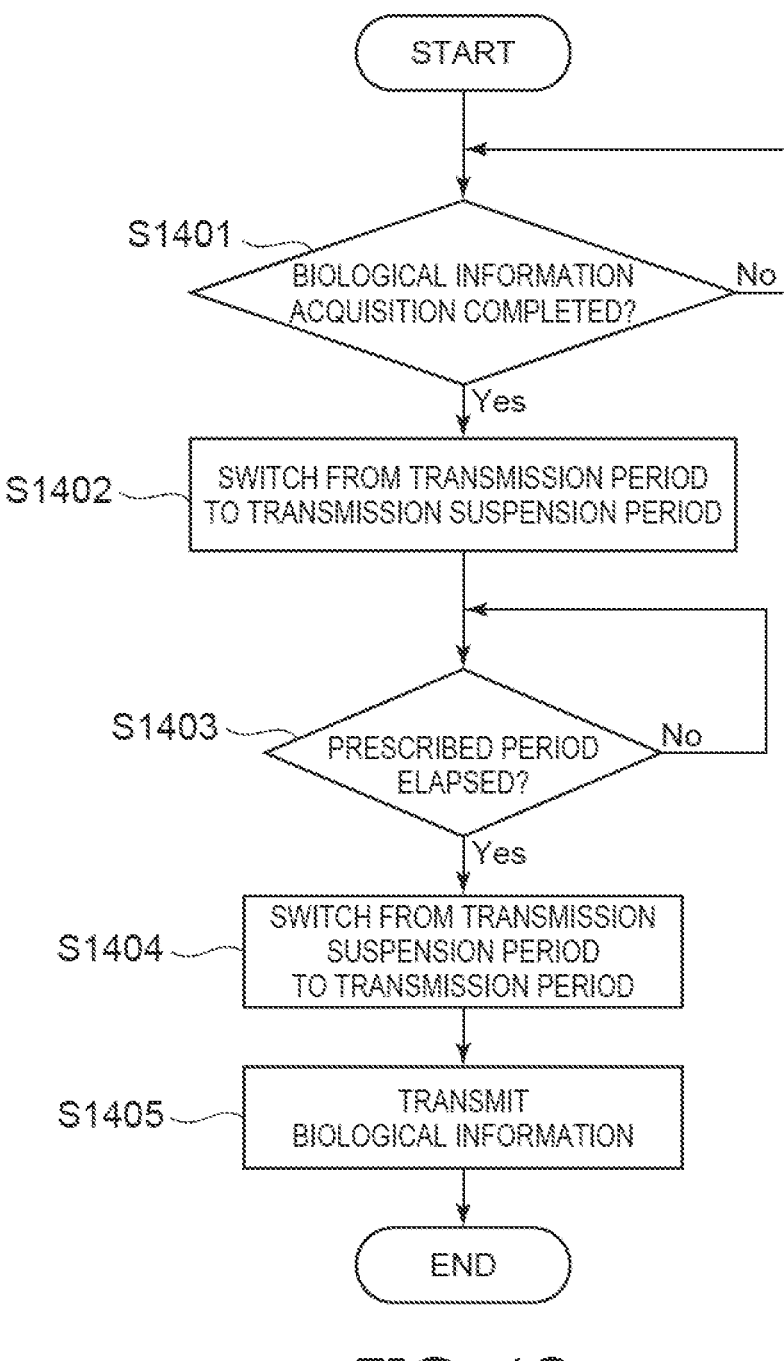
FIG. 13 is a flowchart illustrating an example of the operation of the transmission of the activation signal of the toilet device according to the embodiment.

FIG. 13 is a flowchart illustrating an example of the operation of the transmission of the activation signal of the toilet device according to the embodiment.

As illustrated in FIGS. 12 and 13, in the operation of the use mode, the controller 30 determines whether or not the acquisition of the biological information by the biological information measuring part 20 is completed (step S1401). The controller 30 repeats step S1401 until the acquisition of the biological information is completed. The completion of the acquisition of the biological information is the completion of the acquisition of the measurement information (when the toilet device 100 does not perform the analysis) or the completion of the acquisition of the analysis information. In other words, the completion of the acquisition of the biological information is the completion of the analysis of the analysis information based on the measurement information.

The controller 30 switches from the transmission period to the transmission suspension period in response to the biological information measuring part 20 completing the acquisition of the biological information (step S1402, timing t11). In other words, the controller 30 suspends the transmission of the activation signal in response to the completion of the acquisition of the biological information. Thus, the controller 30 provides the transmission suspension period between the start of the user using the toilet unit 10 and the transmission of the biological information.

The switching to the transmission suspension period may be performed immediately after the completion of the acquisition of the biological information, or may be performed when the prescribed period has elapsed from the completion of the acquisition of the biological information. Thus, the switching to the transmission suspension period in response to the completion of the acquisition of the biological information includes switching at the timing at which the acquisition of the biological information is completed, and switching at the timing at which the prescribed period has elapsed from the completion of the acquisition of the biological information.

After switching to the transmission suspension period, the controller 30 determines whether or not the prescribed period has elapsed from the timing of the switching to the transmission suspension period (step S1403). The prescribed period is, for example, not more than 10 minutes. The prescribed period is more favorably not more than 1 minute. The prescribed period is set to the time necessary to resolve the state in which the personal digital assistant 200 does not respond to the activation signal. It is favorable to set the prescribed period as short as possible while being not less than the time necessary to resolve the state in which the personal digital assistant 200 does not respond to the activation signal.

The controller 30 switches from the transmission suspension period to the transmission period in response to the prescribed period being determined to have elapsed (step S1404, timing t12). In other words, the controller 30 restarts the transmission of the activation signal when the prescribed period has elapsed from the transmission suspension of the activation signal. In other words, the controller 30 switches from the transmission period to the transmission suspension period for a prescribed period in response to the biological information measuring part 20 completing the acquisition of the biological information.

After switching to the transmission period, the controller 30 transmits the biological information to the personal digital assistant 200 of the user in response to the detection of the user leaving the toilet seat 12, etc., as described above (step S1405). Thus, the controller 30 sets the transmission period when transmitting the biological information.

When the biological information measuring part 20 includes multiple sensors, and the multiple sensors need different amounts of time to complete the acquisition of the biological information (for measurement and analysis), the controller 30 may switch from the transmission period to the transmission suspension period for a prescribed period and transmit the biological information each time a sensor completes the acquisition of the biological information. Or, the controller 30 may collectively transmit all of the biological information to the personal digital assistant 200 by switching from the transmission period to the transmission suspension period for a prescribed period when all of the biological information has been acquired.

In the toilet device 100 according to the embodiment as described above, the controller 30 provides the transmission suspension period between the start of the user using the toilet unit 10 and the transmission of the biological information. As a result, the state in which the personal digital assistant 200 does not respond to the activation signal can be resolved by the transmission suspension period, even when a task-kill is performed before the biological information is transmitted. Accordingly, when transmitting the biological information, the undesirable state in which the personal digital assistant 200 does not respond to the activation signal can be suppressed. By setting the transmission period when transmitting the biological information, the personal digital assistant 200 can be switched more appropriately to the active state when transmitting the biological information; and the biological information can be transmitted more appropriately and automatically to the personal digital assistant 200 via wireless communication. As a result, the need for the user to take action such as moving once out of the range of communication or manually establishing wireless communication can be suppressed, and the usability can be further improved.

In the toilet device 100 according to the embodiment, the controller 30 switches from the transmission period to the transmission suspension period for a prescribed period in response to the biological information measuring part 20 completing the acquisition of the biological information. As a result, the undesirable state in which the personal digital assistant 200 does not respond to the activation signal when transmitting the biological information due to a task-kill performed before the biological information is transmitted can be more appropriately suppressed.

The timing of switching from the transmission period to the transmission suspension period is not limited to the timing of the completion of the acquisition of the biological information, and may be any timing related to the start of the user using the toilet unit 10. The timing of the start of the user using the toilet unit 10 may be, for example, the timing at which the proximity sensor 62 detects the user approaching the toilet unit 10 (entering the toilet room TR), the timing at which the seating sensor 61 detects the user being seated on the toilet seat 12, the timing at which a signal (e.g., the authentication signal) is received from the remote control 70, or the timing at which the wireless communication with the personal digital assistant 200 is established.

Figure 14:
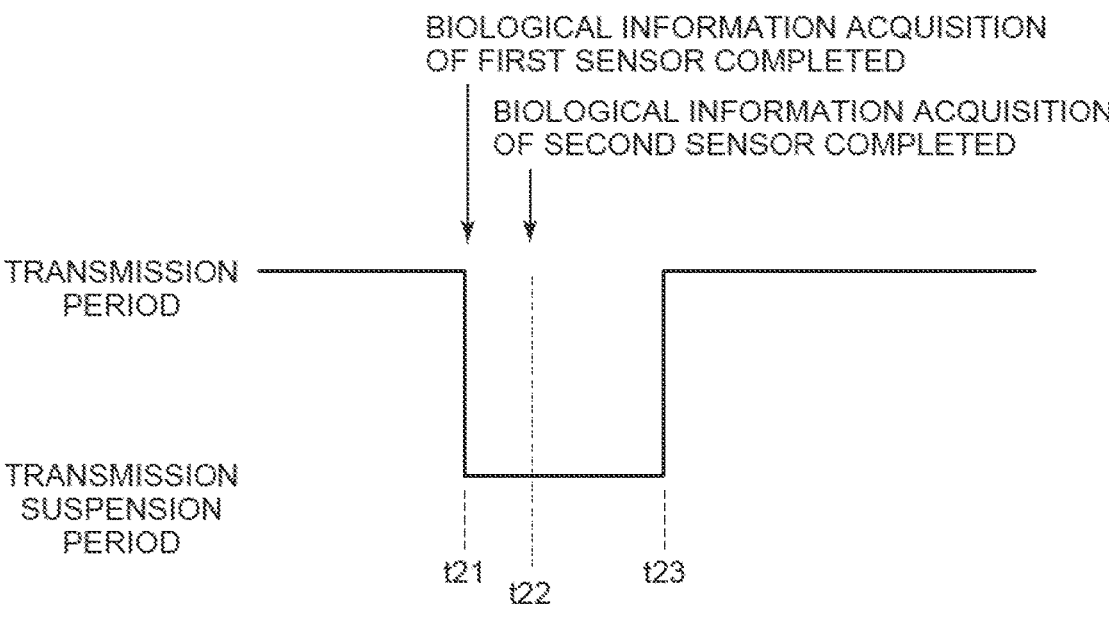
FIG. 14 is a timing chart illustrating a modification of the operation of the transmission of the activation signal of the toilet device according to the embodiment.

FIG. 14 is a timing chart illustrating a modification of the operation of the transmission of the activation signal of the toilet device according to the embodiment.

When the biological information measuring part 20 includes multiple sensors, there is a possibility that amounts of time for the multiple sensors to complete the acquisition of the biological information may change. In such a case, when the transmission period is switched to the transmission suspension period for a prescribed period each time a sensor completes the acquisition of the biological information, and when the transmission period is switched to the transmission suspension period in response to one sensor completing the acquisition of the biological information, it is possible that another sensor may complete the acquisition of the biological information during the transmission suspension period.

In such a case, when the other sensor completes the acquisition of the biological information during the transmission suspension period as illustrated in FIG. 14, the controller 30 starts timing the prescribed period from the timing at which the other sensor completes the acquisition of the biological information.

In the example illustrated in FIG. 14, the controller 30 switches from the transmission period to the transmission suspension period in response to the first sensor 21 completing the acquisition of the biological information (the timing t21), starts timing the prescribed period in response to the detection of the second sensor 22 completing the acquisition of the biological information during the transmission suspension period (the timing t22), and switches from the transmission suspension period to the transmission period when a prescribed period has elapsed from the second sensor 22 completing the acquisition of the biological information (the timing t23).

Thus, when the other sensor completes the acquisition of the biological information during the transmission suspension period, the controller 30 starts timing the prescribed period from the timing at which the other sensor completes the acquisition of the biological information. For example, the state in which the personal digital assistant 200 does not respond to the activation signal can be more appropriately resolved thereby. When the other sensor completes the acquisition of the biological information during the transmission suspension period, the controller 30 may switch from the transmission suspension period to the transmission period when a prescribed period has elapsed from a previous sensor completing the acquisition of the biological information.

Figure 15:
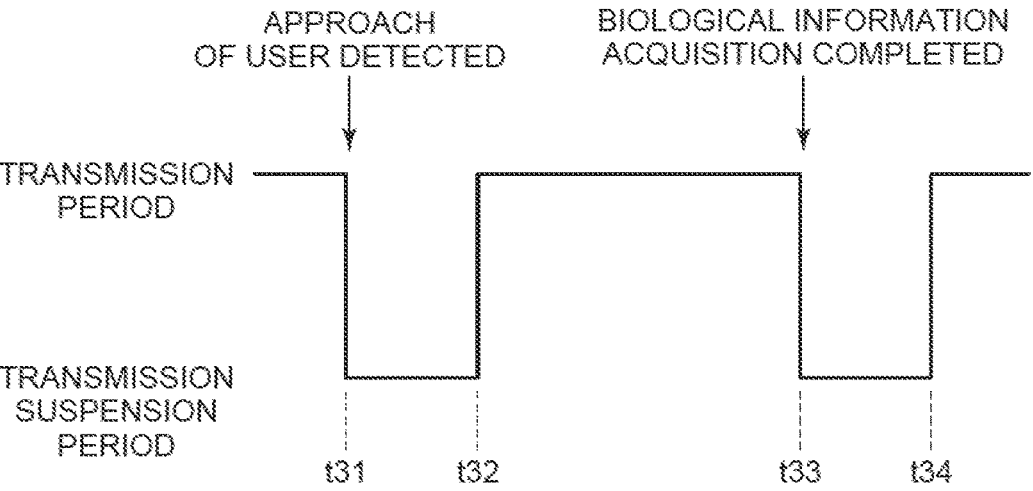
FIG. 15 is a timing chart illustrating a modification of the operation of the transmission of the activation signal of the toilet device according to the embodiment.

FIG. 15 is a timing chart illustrating a modification of the operation of the transmission of the activation signal of the toilet device according to the embodiment.

Figure 16:
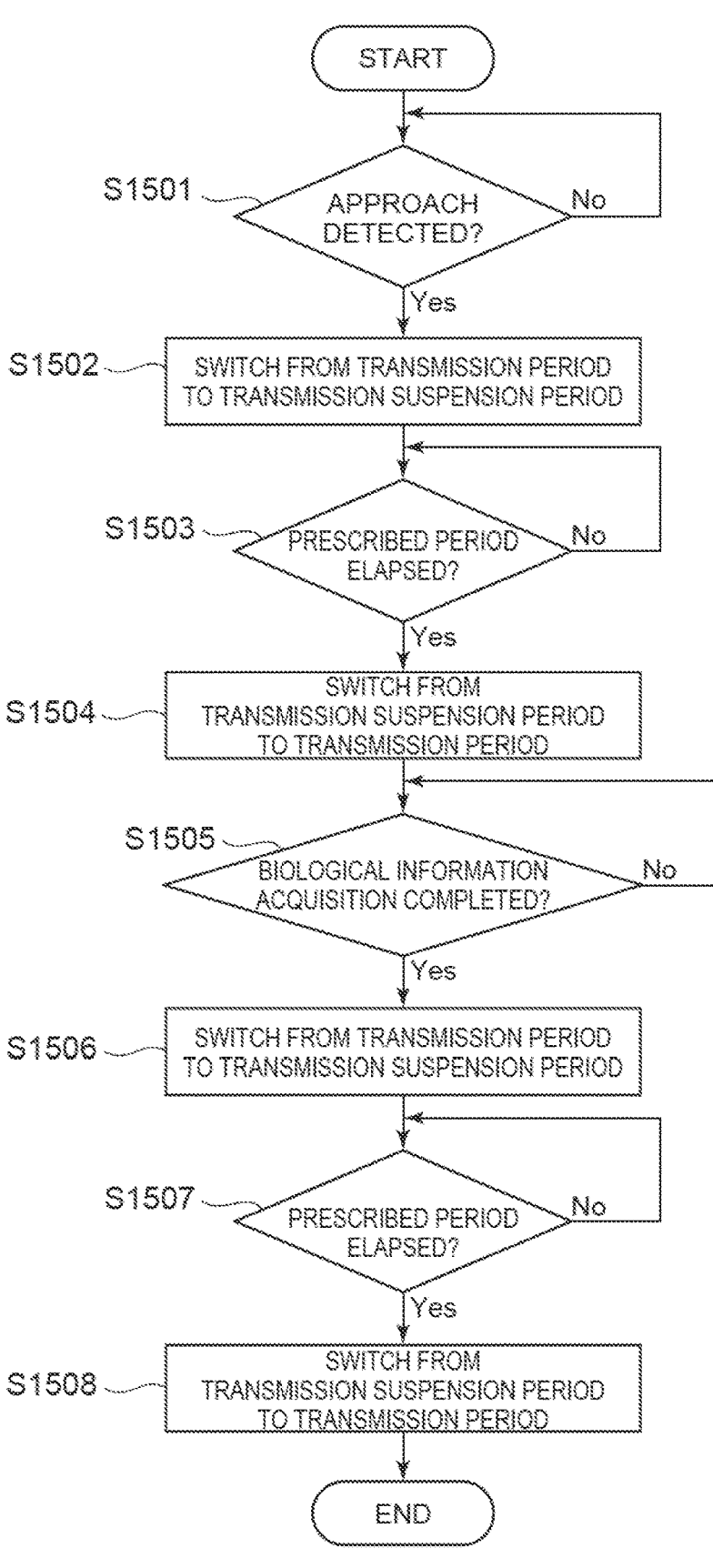
FIG. 16 is a flowchart illustrating the modification of the operation of the transmission of the activation signal of the toilet device according to the embodiment.

FIG. 16 is a flowchart illustrating the modification of the operation of the transmission of the activation signal of the toilet device according to the embodiment.

In the example as illustrated in FIGS. 15 and 16, the controller 30 determines whether or not the proximity sensor 62 has detected the user approaching the toilet unit 10 (entering the toilet room TR) (step S1501).

The controller 30 switches from the transmission period to the transmission suspension period in response to the proximity sensor 62 detecting the user approaching the toilet unit 10 (step S1502, timing t31). In other words, the controller 30 suspends the transmission of the activation signal in response to the proximity sensor 62 detecting the user approaching the toilet unit 10. The switching to the transmission suspension period may be performed immediately after the approach is detected, or may be performed when a prescribed period has elapsed from the approach being detected.

After switching to the transmission suspension period, the controller 30 determines whether or not a prescribed period has elapsed from the timing of the switching to the transmission suspension period (step S1503).

When it is determined that the prescribed period has elapsed, the controller 30 switches from the transmission suspension period to the transmission period (step S1504, timing t32). In other words, in the example, the controller 30 switches from the transmission period to the transmission suspension period for a prescribed period in response to the proximity sensor 62 detecting the user approaching the toilet unit 10.

Thereafter, similarly to the description related to FIGS. 12 and 13, the controller 30 switches from the transmission period to the transmission suspension period for a prescribed period in response to the biological information measuring part 20 completing the acquisition of the biological information (steps S1505 to S1508, timing t33 and t34).

Thus, in the example, by switching from the transmission period to the transmission suspension period for a prescribed period in response to the proximity sensor 62 detecting the user approaching, the personal digital assistant 200 can be switched more promptly to the active state. For example, the state in which the personal digital assistant 200 does not respond to the activation signal when switching the personal digital assistant 200 to the active state to perform the user authentication can be resolved by the transmission suspension period; and the establishment of wireless communication can be started more appropriately and automatically. By switching from the transmission period to the transmission suspension period for a prescribed period in response to the completion of the acquisition of the biological information, the undesirable state in which the personal digital assistant 200 does not respond to the activation signal when transmitting the biological information can be suppressed, even when a task-kill is performed between detecting the approach and completing the acquisition of the biological information.

Figure 17:
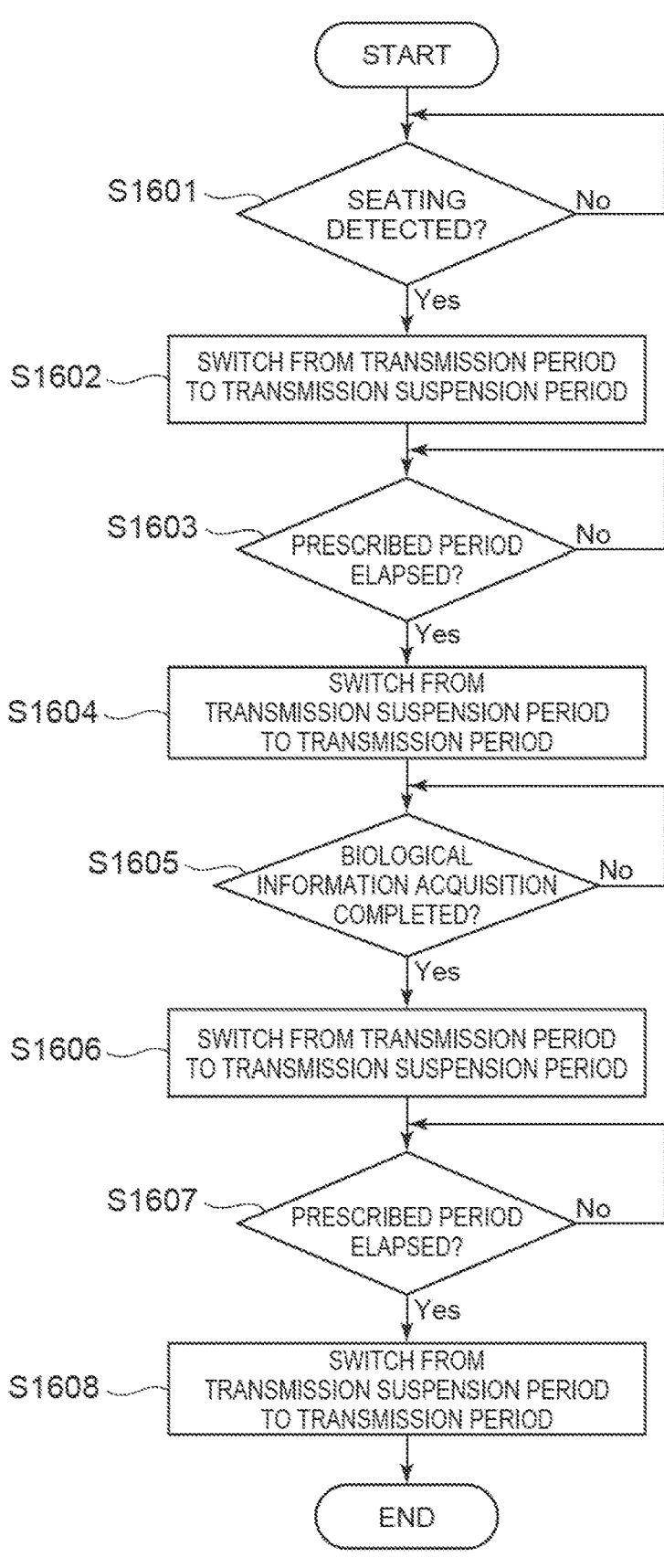
FIG. 17 is a flowchart illustrating a modification of the operation of the transmission of the activation signal of the toilet device according to the embodiment.

FIG. 17 is a flowchart illustrating a modification of the operation of the transmission of the activation signal of the toilet device according to the embodiment.

In the example as illustrated in FIG. 17, the controller 30 determines whether or not the seating sensor 61 has detected the user being seated on the toilet seat 12 (step S1601).

The controller 30 switches from the transmission period to the transmission suspension period in response to the seating sensor 61 detecting the user being seated (step S1602). In other words, the controller 30 suspends the transmission of the activation signal in response to the seating sensor 61 detecting the user being seated on the toilet seat 12. The switching to the transmission suspension period may be performed immediately after the seating is detected, or may be performed when a prescribed period has elapsed from the seating being detected.

After switching to the transmission suspension period, the controller 30 determines whether or not a prescribed period has elapsed from the timing of the switching to the transmission suspension period (step S1603).

When it is determined that the prescribed period has elapsed, the controller 30 switches from the transmission suspension period to the transmission period (step S1604). In other words, in the example, the controller 30 switches from the transmission period to the transmission suspension period for a prescribed period in response to the seating sensor 61 detecting the user being seated.

Thereafter, similarly to the description related to FIGS. 12 and 13, the controller 30 switches from the transmission period to the transmission suspension period for a prescribed period in response to the biological information measuring part 20 completing the acquisition of the biological information (steps S1605 to S1608).

Thus, in the example, by switching from the transmission period to the transmission suspension period for a prescribed period in response to the seating sensor 61 detecting the user being seated, the personal digital assistant 200 can be switched more promptly to the active state. For example, the state in which the personal digital assistant 200 does not respond to the activation signal when switching the personal digital assistant 200 to the active state to perform the user authentication can be resolved by the transmission suspension period; and the establishment of wireless communication can be started more appropriately and automatically. By switching from the transmission period to the transmission suspension period for a prescribed period in response to the completion of the acquisition of the biological information, the undesirable state in which the personal digital assistant 200 does not respond to the activation signal when transmitting the biological information can be suppressed, even when a task-kill is performed between detecting the approach and completing the acquisition of the biological information.

Method for Controlling Toilet Device

According to an embodiment, a method for controlling the toilet device 100 is provided. As illustrated in FIGS. 4 to 17, the method for controlling the toilet device 100 according to the embodiment includes a process of providing the transmission suspension period between the start of the user using the toilet unit 10 and the transmission of the biological information, and setting the transmission period when the biological information is transmitted. As a result, the biological information can be more appropriately transmitted to the personal digital assistant 200 of the user via wireless communication.

Control Program of Toilet Device

According to the embodiment, a control program that is installed in the toilet device 100 is provided. As illustrated in FIGS. 4 to 17, the control program of the toilet device 100 according to the embodiment causes the toilet device 100 to perform a process of providing the transmission suspension period between the start of the user using the toilet unit 10 and the transmission of the biological information, and setting the transmission period when the biological information is transmitted. As a result, the biological information can be more appropriately transmitted to the personal digital assistant 200 of the user via wireless communication. For example, the control program is stored in the storage part 50. The controller 30 performs the process described above by reading the control program stored in the storage part 50 and by sequentially processing the control program. For example, the control program may be stored in internal memory of the controller 30, etc.

Recording Medium

According to an embodiment, a recording medium is provided in which the control program of the toilet device described above is recorded. The recording medium is readable by at least a computer. The recording medium may be read-only, or may be both readable and writable.

Embodiments may include the following configurations.

Configuration 1

A toilet device, comprising:
a toilet unit including a toilet seat;
a biological information measuring part configured to measure biological information of a user;
a wireless communication part configured to wirelessly communicate with a personal digital assistant of the user; and
a controller configured to transmit the biological information to the personal digital assistant of the user,
the personal digital assistant including
    an active state in which an application software is activated, and
    an inactive state in which the application software is suspended,
the personal digital assistant being configured to receive the biological information by wirelessly communicating with the wireless communication part in the active state,
the controller being configured to
    allow the biological information to be automatically transmitted to the personal digital assistant by switching the personal digital assistant from the inactive state to the active state by transmitting an activation signal from the wireless communication part to the personal digital assistant, the activation signal being for switching the personal digital assistant from the inactive state to the active state,
    control switching between a transmission period and a transmission suspension period, the activation signal being transmitted in the transmission period, the transmission of the activation signal being suspended in the transmission suspension period,
    provide the transmission suspension period between a start of the user using the toilet unit and a transmission of the biological information, and
    set the transmission period when transmitting the biological information.

Configuration 2

The toilet device according to configuration 1, wherein the controller switches from the transmission period to the transmission suspension period for a prescribed period in response to the biological information measuring part completing an acquisition of the biological information.

Configuration 3

The toilet device according to configuration 2, further comprising:
    a proximity sensor configured to detect the user approaching the toilet unit and the user leaving the toilet unit,
    the controller switching from the transmission period to the transmission suspension period for a prescribed period in response to the proximity sensor detecting the user approaching.

Configuration 4

The toilet device according to configuration 2, further comprising:
    a seating sensor configured to detect the user being seated on the toilet seat and the user leaving the toilet seat,
    the controller switching from the transmission period to the transmission suspension period for a prescribed period in response to the seating sensor detecting the user being seated.

Configuration 5

A method for controlling a toilet device,
the toilet device comprising:
    a toilet unit including a toilet seat;
    a biological information measuring part configured to measure biological information of a user;
    a wireless communication part configured to wirelessly communicate with a personal digital assistant of the user; and
    a controller configured to transmit the biological information to the personal digital assistant of the user,
the personal digital assistant including:
    an active state in which an application software is activated; and
    an inactive state in which the application software is suspended,
the personal digital assistant being configured to receive the biological information by wirelessly communicating with the wireless communication part in the active state, the controller being configured to:

allow the biological information to be automatically transmitted to the personal digital assistant by switching the personal digital assistant from the inactive state to the active state by transmitting an activation signal from the wireless communication part to the personal digital assistant, the activation signal being for switching the personal digital assistant from the inactive state to the active state; and control switching between a transmission period and a transmission suspension period, the activation signal being transmitted in the transmission period, the transmission of the activation signal being suspended in the transmission suspension period, the method comprising:

providing the transmission suspension period between a start of the user using the toilet unit and a transmission of the biological information, and setting the transmission period when the biological information is transmitted.

Configuration 6

A control program of a toilet device, the control program being installed in the toilet device, the toilet device comprising:

a toilet unit including a toilet seat;

a biological information measuring part configured to measure biological information of a user;

a wireless communication part configured to wirelessly communicate with a personal digital assistant of the user; and a controller configured to transmit the biological information to the personal digital assistant of the user, the personal digital assistant including:

an active state in which an application software is activated; and an inactive state in which the application software is suspended, the personal digital assistant being configured to receive the biological information by wirelessly communicating with the wireless communication part in the active state, the controller being configured to:

allow the biological information to be automatically transmitted to the personal digital assistant by switching the personal digital assistant from the inactive state to the active state by transmitting an activation signal from the wireless communication part to the personal digital assistant, the activation signal being for switching the personal digital assistant from the inactive state to the active state; and control switching between a transmission period and a transmission suspension period, the activation signal being transmitted in the transmission period, the transmission of the activation signal being suspended in the transmission suspension period, the control program being configured to cause the toilet device to provide the transmission suspension period between a start of the user using the toilet unit and a transmission of the biological information, and to set the transmission period when the biological information is transmitted.

Thus, according to embodiments, a toilet device, a method for controlling a toilet device, and a control program of a toilet device are provided in which biological information can be more appropriately transmitted to the personal digital assistant 200 of a user via wireless communication.

The invention has been described with reference to the embodiments. However, the invention is not limited to these embodiments. Any design changes in the above embodiments suitably made by those skilled in the art are also encompassed within the scope of the invention as long as they fall within the spirit of the invention. For example, the shape, the size the material, the disposition and the arrangement or the like of the components included in the toilet device are not limited to illustrations and can be changed appropriately.

The components included in the embodiments described above can be combined to the extent possible, and these combinations are also encompassed within the scope of the invention as long as they include the features of the invention.

What is claimed is:

1. A toilet device, comprising:

a toilet unit including a toilet seat;

a biological information measuring part configured to measure biological information of a user;

a wireless communication part configured to wirelessly communicate with a personal digital assistant of the user; and a controller configured to transmit the biological information to the personal digital assistant of the user, the personal digital assistant including an active state in which an application software is activated, and an inactive state in which the application software is suspended, the personal digital assistant being configured to receive the biological information by wirelessly communicating with the wireless communication part in the active state, the controller being configured to allow the biological information to be automatically transmitted to the personal digital assistant by switching the personal digital assistant from the inactive state to the active state by transmitting an activation signal from the wireless communication part to the personal digital assistant, the activation signal being for switching the personal digital assistant from the inactive state to the active state, control switching between a transmission period and a transmission suspension period, the activation signal being transmitted in the transmission period, the transmission of the activation signal being suspended in the transmission suspension period, provide the transmission suspension period between a start of the user using the toilet unit and a transmission of the biological information, and set the transmission period when transmitting the biological information.

2. The toilet device according to claim 1, wherein the controller switches from the transmission period to the transmission suspension period for a prescribed period in response to the biological information measuring part completing an acquisition of the biological information.

3. The toilet device according to claim 2, further comprising:

a proximity sensor configured to detect the user approaching the toilet unit and the user leaving the toilet unit, the controller switching from the transmission period to the transmission suspension period for a prescribed period in response to the proximity sensor detecting the user approaching.

4. The toilet device according to claim 2, further comprising:

a seating sensor configured to detect the user being seated on the toilet seat and the user leaving the toilet seat, the controller switching from the transmission period to the transmission suspension period for a prescribed period in response to the seating sensor detecting the user being seated.

5. A method for controlling a toilet device, the toilet device comprising:

a toilet unit including a toilet seat;

a biological information measuring part configured to measure biological information of a user;

a wireless communication part configured to wirelessly communicate with a personal digital assistant of the user; and a controller configured to transmit the biological information to the personal digital assistant of the user, the personal digital assistant including:

an active state in which an application software is activated; and an inactive state in which the application software is suspended, the personal digital assistant being configured to receive the biological information by wirelessly communicating with the wireless communication part in the active state, the controller being configured to:

allow the biological information to be automatically transmitted to the personal digital assistant by switching the personal digital assistant from the inactive state to the active state by transmitting an activation signal from the wireless communication part to the personal digital assistant, the activation signal being for switching the personal digital assistant from the inactive state to the active state; and control switching between a transmission period and a transmission suspension period, the activation signal being transmitted in the transmission period, the transmission of the activation signal being suspended in the transmission suspension period, the method comprising:

providing the transmission suspension period between a start of the user using the toilet unit and a transmission of the biological information, and setting the transmission period when the biological information is transmitted.

6. A non-transitory computer-readable storage medium, comprising:

a control program stored in the non-transitory computer-readable storage medium, the non-transitory computer-readable storage medium being provided in a toilet device, the toilet device comprising:

a toilet unit including a toilet seat;

a biological information measuring part configured to measure biological information of a user;

a wireless communication part configured to wirelessly communicate with a personal digital assistant of the user; and a controller configured to transmit the biological information to the personal digital assistant of the user, the personal digital assistant including:

an active state in which an application software is activated; and an inactive state in which the application software is suspended, the personal digital assistant being configured to receive the biological information by wirelessly communicating with the wireless communication part in the active state, the controller being configured to:

allow the biological information to be automatically transmitted to the personal digital assistant by switching the personal digital assistant from the inactive state to the active state by transmitting an activation signal from the wireless communication part to the personal digital assistant, the activation signal being for switching the personal digital assistant from the inactive state to the active state; and control switching between a transmission period and a transmission suspension period, the activation signal being transmitted in the transmission period, the transmission of the activation signal being suspended in the transmission suspension period, the control program being configured to cause the toilet device to provide the transmission suspension period between a start of the user using the toilet unit and a transmission of the biological information, and to set the transmission period when the biological information is transmitted.

* * * * *